United States Patent
Zhang et al.

(10) Patent No.: US 11,574,716 B2
(45) Date of Patent: Feb. 7, 2023

(54) SYSTEM AND METHOD FOR GENERATING IMAGING REPORT

(71) Applicant: SHANGHAI UNITED IMAGING HEALTHCARE CO., LTD., Shanghai (CN)

(72) Inventors: Zheng Zhang, Shanghai (CN); Hui Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 102 days.

(21) Appl. No.: 16/679,446

(22) Filed: Nov. 11, 2019

(65) Prior Publication Data
US 2020/0303049 A1    Sep. 24, 2020

(30) Foreign Application Priority Data
Mar. 22, 2019  (CN) .......................... 201910222052.6

(51) Int. Cl.
*G16H 15/00*   (2018.01)
*G06T 7/33*    (2017.01)
(Continued)

(52) U.S. Cl.
CPC ............. *G16H 15/00* (2018.01); *G06N 20/00* (2019.01); *G06T 7/0014* (2013.01); *G06T 7/337* (2017.01);
(Continued)

(58) Field of Classification Search
CPC ........ G16H 15/00; G16H 30/20; G16H 30/40; G16H 50/20; G16H 30/00; G06T 7/337;
(Continued)

(56) References Cited

U.S. PATENT DOCUMENTS

| | | | |
|---|---|---|---|
| 2005/0123185 A1 | 6/2005 | Balasubramanian et al. | |
| 2010/0099974 A1* | 4/2010 | Desai | G16H 15/00 707/708 |
| 2011/0229005 A1* | 9/2011 | Den Harder | G06T 7/11 382/128 |
| 2015/0018666 A1* | 1/2015 | Madabhushi | A61B 18/20 600/411 |

(Continued)

FOREIGN PATENT DOCUMENTS

| | | | |
|---|---|---|---|
| CN | 1378677 A | 11/2002 | |
| CN | 1615489 | * 5/2005 | ......... G06F 16/5838 |

(Continued)

*Primary Examiner* — Amara Abdi
(74) *Attorney, Agent, or Firm* — Metis IP LLC

(57) ABSTRACT

The present disclosure provides a system and a method for generating an imaging report. The method may include obtaining first imaging information and second imaging information. The first and second imaging information may be acquired from an examination region of a subject using a first imaging device or a second imaging device, respectively. The method may include identifying at least one first target ROI based on the first imaging information, and determining first reporting information corresponding to the at least one first target ROI. The method may include identifying at least one second target ROI with respect to the second imaging information based on the at least one first target ROI, and determining second reporting information corresponding to the at least one second target ROI. The method may further include generating a report based on at least a part of the first reporting information or the second reporting information.

17 Claims, 14 Drawing Sheets

(51) Int. Cl.
*G16H 30/20* (2018.01)
*G16H 30/40* (2018.01)
*G06N 20/00* (2019.01)
*G06T 7/00* (2017.01)
*G06V 10/25* (2022.01)

(52) U.S. Cl.
CPC ............ *G06V 10/25* (2022.01); *G16H 30/20* (2018.01); *G16H 30/40* (2018.01); *G06T 2207/20081* (2013.01); *G06T 2207/20221* (2013.01)

(58) Field of Classification Search
CPC ......... G06T 7/0014; G06T 2207/20081; G06T 2207/20221; G06N 20/00; G06K 9/3233; G06K 9/6288; G06K 2009/2045; G06K 2209/05; G06K 9/6273
See application file for complete search history.

(56) References Cited

U.S. PATENT DOCUMENTS

| | | | | |
|---|---|---|---|---|
| 2017/0079608 | A1* | 3/2017 | Hamill | A61B 6/032 |
| 2019/0139218 | A1* | 5/2019 | Song | G06F 16/50 |
| 2021/0042924 | A1* | 2/2021 | Miyasa | A61B 6/03 |

FOREIGN PATENT DOCUMENTS

| | | | | |
|---|---|---|---|---|
| CN | 1615489 | A | 5/2005 | |
| CN | 1886745 | * | 12/2006 | ............... G06T 7/00 |
| CN | 1886745 | A | 12/2006 | |
| CN | 108324246 | A | 7/2016 | |
| CN | 106909778 | * | 6/2017 | ............ G16H 50/20 |
| CN | 106909778 | A | 6/2017 | |
| CN | 107463786 | * | 12/2017 | |
| CN | 107463786 | A | 12/2017 | |
| CN | 108376558 | A | 8/2018 | |

* cited by examiner

SYSTEM AND METHOD FOR GENERATING IMAGING REPORT

CROSS-REFERENCE TO RELATED APPLICATIONS

This application claims priority to Chinese Application No. 201910222052.6 filed on Mar. 22, 2019, the contents of which are hereby incorporated by reference.

TECHNICAL FIELD

This disclosure generally relates to systems and methods for imaging, and more particularly, to systems and methods for generating a diagnostic imaging report.

BACKGROUND

At present, multiple medical imaging devices may be used to identify and analyze lesions. For example, a positron emission computed tomography (PET) scanner may be used to acquire molecular functional information of the lesion, and a computed tomography (CT) scanner may be used to acquire anatomical information of the lesion. In this case, a multi-modality medical imaging device that integrates two or more imaging devices may be used to identify and/or analyze the lesion. For example, a PET-CT system that combines a PET scanner with a CT scanner may acquire physiological metabolism of tissue of a human body through radioactive nuclides, and anatomical information of the tissue using the CT technology. As another example, a PET-MR system that combines a PET scanner with an MR scanner may acquire anatomical information as well as physiological metabolism information.

Existing multi-modality devices may need a doctor to analyze one or more images of a region of interest (ROI) manually, identify a lesion based on the ROI, and/or provide a description regarding characteristics of the lesions, etc., in order to generate a diagnostic imaging report. However, since a large amount of data is provided by such multi-modality devices, it may be difficult for doctors to integrate the large amount of data in a short period of time. In addition, the doctors may also need to have knowledge and/or experience with various medical image interpretation skills associated with such multi-modality devices, thus increasing labor costs. Furthermore, conventional report generation techniques may have a low efficiency and high operating costs, and need a lot of interventions from operators. Thus, it is desirable to provide efficient and comprehensive systems and methods for generating medical imaging reports for a multi-modality imaging device.

SUMMARY

According to one aspect of the present disclosure, a method implemented on a computing apparatus having at least one processor and at least one computer-readable storage device is provided. The method may include obtaining first imaging information and second imaging information. The first imaging information may be acquired from an examination region of a subject using a first imaging device, and the second imaging information may be acquired from the examination region of the subject using a second imaging device. The method may include identifying at least one first target ROI based on the first imaging information, and determining first reporting information corresponding to the at least one first target ROI. The method may include identifying at least one second target ROI with respect to the second imaging information based on the at least one first target ROI, and determining second reporting information corresponding to the at least one second target ROI. The method may further include generating a report based on at least a part of the first reporting information or the second reporting information.

In some embodiments, the method may include receiving third reporting information input by a user through a user interface, and updating the report based on the third report information.

In some embodiments, the identifying at least one first target ROI based on the first imaging information may include determining at least two candidate ROIs based on the first imaging information and an image recognition technique, and receiving a region selection instruction from a user. The identifying at least one first target ROI based on the first imaging information may further include selecting the at least one first target ROI from the at least two candidate ROIs based on the region selection instruction.

In some embodiments, the method may include causing a certain region of the subject to be displayed in a first displaying area of a reporting interface. The method may include causing the at least two candidate ROIs to be displayed in the first displaying area and a first interaction area of the reporting interface. The method may include causing at least a portion of the first imaging information and the second imaging information to be displayed in a second interaction area of the reporting interface in response to the region selection instruction. The at least a portion of the first imaging information and the second imaging information may include information corresponding to the certain region of the subject. The method may further include causing the report to be displayed in a report displaying area in the reporting interface.

In some embodiments, the method may include designating one or more regions in the at least two candidate ROIs other than the selected at least one first target ROI as filtered-out regions. The method may further include generating a first target ROI determination model by training a preliminary model based on the filtered-out regions and at least one first target ROI.

In some embodiments, the method may include determining characteristics of signals related to the filtered-out regions and at least one first target ROI. The method may further include training the preliminary machine learning model based on the characteristics of signals related to the filtered-out regions and at least one first target ROI.

In some embodiments, the identifying at least one first target ROI in the scanning region based on the first imaging information may include determining at least two candidate ROIs in the scanning region based on the first imaging information and an image recognition technique, and determining the at least one first target ROI by inputting the at least two candidate ROIs into a first target ROI determination model.

In some embodiments, the obtaining first imaging information may include obtaining original imaging information, and determining the first imaging information in the original imaging information according to a filtering rule input by a user. The original imaging information may be acquired from the examination region of the subject using the first imaging device.

In some embodiments, the first imaging information may reflect molecular functional information of the examination region, and the second imaging information may reflect anatomical information of the examination region.

In some embodiments, the first imaging device may include a positron emission computed tomography (PET) scanner or a single-photon emission computed tomography (SPECT) scanner, and the second imaging device may include a computed tomography (CT) scanner or a magnetic resonance (MR) scanner.

In some embodiments, the first imaging information and the second imaging information may be with respect to a same coordinate system.

In some embodiments, the identifying at least one second target ROI with respect to the second imaging information based on the at least one first target ROI may include performing an image fusion or an image registration between the first imaging information and the second imaging information according to the same coordinate system. The identifying at least one second target ROI with respect to the second imaging information based on the at least one first target ROI may further include identifying at least one ROI associated with the at least one first target ROI in the second imaging information, and designating the identified at least one ROI associated with the at least one first target ROI as the at least one second target ROI.

In some embodiments, the report may include at least one of an image, text, a video, or an annotation.

According to another aspect of the present disclosure, a system is provided. The system may include at least one storage device storing a set of instructions, and at least one processor configured to communicate with the at least one storage device. When executing the set of instructions, the at least one processor may be configured to cause the system to perform the following operations. The at least one processor may be configured to cause the system to obtain first imaging information and second imaging information. The first imaging information may be acquired from an examination region of a subject using a first imaging device, and the second imaging information may be acquired from the examination region of the subject using a second imaging device. The at least one processor may be configured to cause the system to identify at least one first target ROI based on the first imaging information, and determine first reporting information corresponding to the at least one first target ROI. The at least one processor may be configured to cause the system to identify at least one second target ROI with respect to the second imaging information based on the at least one first target ROI, and determine second reporting information corresponding to the at least one second target ROI. The at least one processor may be further configured to cause the system to generate a report based on at least a part of the first reporting information or the second reporting information.

According to still another aspect of the present disclosure, a device is provided. The device may include at least one storage device storing a set of instructions, and at least one processor configured to communicate with the at least one storage device. When executing the set of instructions, the at least one processor may be configured to cause the device to perform the following operations. The at least one processor may be configured to cause the device to obtain first imaging information and second imaging information. The first imaging information may be acquired from an examination region of a subject using a first imaging device, and the second imaging information may be acquired from the examination region of the subject using a second imaging device. The at least one processor may be also configured to cause the device to identify at least one first target ROI based on the first imaging information, and identify at least one second target ROI with respect to the second imaging information based on the at least one first target ROI. The at least one processor may be further configured to cause the device to generate a report based on at least a part of the first reporting information or the second reporting information.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
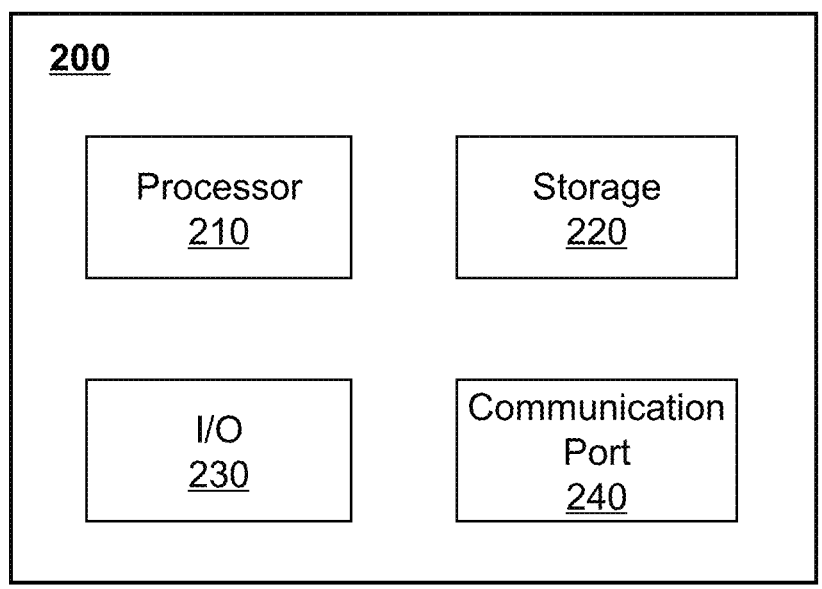
FIG. 2 is a schematic diagram illustrating hardware and/or software components of an exemplary computing apparatus 200 on which the processing device 120 may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on one or more computing apparatuses (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing apparatus, for execution by the computing apparatus. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing apparatus functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood the operations of the flowchart may be implemented not in order. Conversely, the operations may be implemented in inverted order, or simultaneously. Moreover, one or more other operations may be added to the flowcharts. One or more operations may be removed from the flowcharts.

Aspects of the present disclosure relate to methods and systems for generating a diagnostic imaging report for a scan performed by a multi-modality imaging device. After first imaging information of a subject acquired using a first modality device (e.g., PET scanner) and second imaging information of the subject acquired using a second modality device (e.g., CT scanner) is obtained, at least one first target ROI with respect to the first imaging information may be identified, and first reporting information corresponding to the at least one first target ROI may be determined. At least one second target ROI with respect to the second imaging information corresponding to the at least one first target ROI may be identified, and second reporting information corresponding to the at least one second target ROI may be determined. The diagnostic imaging report may be determined based on the first reporting information and/or the second reporting information.

The present disclosure is directed to provide a convenient way in which imaging report generation functionality can be introduced into an existing main system without the need to modify the main system significantly to form an imaging system configured to generate diagnosis reports. This is achieved by configuring the imaging report generation system 100 as an add-on system that may be integrated or coupled to a main system including at least one imaging modality device. For instance, the imaging report generation system 100 may be configured as supporting software for installing on or incorporating to the main system.

Figure 1:
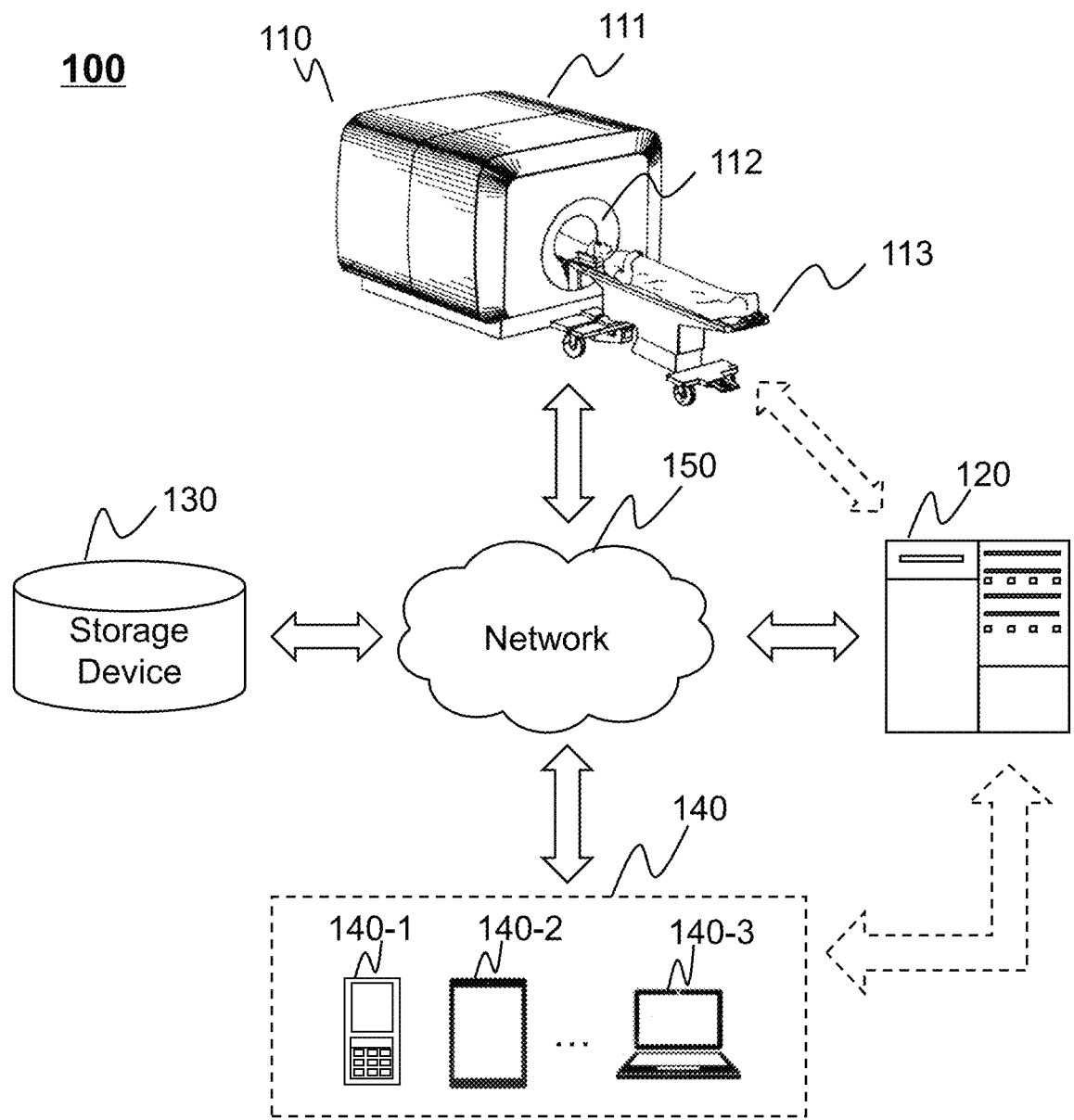
FIG. 1 is a schematic diagram illustrating an exemplary imaging report generation system 100 according to some embodiments of the present disclosure.

FIG. 1 is a schematic diagram illustrating an exemplary imaging report generation system 100 according to some embodiments of the present disclosure. As illustrated, the imaging report generation system 100 may include an imaging scanner 110, a processing device 120, a storage device 130, one or more terminals 140, and a network 150. The components in the imaging report generation system 100 may be connected in various ways. Merely by way of example, as illustrated in FIG. 1, the imaging scanner 110 may be connected to the processing device 120 through the network 150. As another example, the imaging scanner 110 may be connected with the processing device 120 directly as indicated by the bi-directional arrow in dotted lines linking the imaging scanner 110 and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

The imaging scanner 110 may scan a subject or a portion thereof that is located within its detection region, and generate imaging signals relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the heart, the esophagus, the trachea, the bronchus, the stomach, the gallbladder, the small intestine, the colon, the bladder, the ureter, the uterus, the fallopian tube, etc. In some embodiments, the imaging scanner 110 may include a computed tomography (CT) scanner, a positron emission computed tomography (PET) scanner, a single-photon emission computed tomography (SPECT) scanner, a magnetic resonance (MR) scanner, an ultrasonic scanner, an emission computed tomography (ECT) scanner, or the like. In some embodiment, the imaging scanner 110 may be a multi-modality device including two or more scanners listed above. For example, the imaging scanner 110 may be a PET-CT scanner, a PET-MR scanner, etc.

Merely for illustration purposes, a PET-CT scanner may be provided as an example of the imaging scanner 110, which is not intended to limit the scope of the present disclosure. The PET-CT may include a gantry 111, a detecting region 112, and a scanning table 113. The gantry 111 may support one or more radiation sources and/or detectors (not shown). A subject may be placed on the scanning table 113 for CT scan and/or PET scan. The PET-CT scanner may combine a CT scanner with a PET scanner. When the imaging scanner 110 performs a CT scan, a radiation source may emit radioactive rays to the subject, and one or more detectors may detect radiation rays emitted from the detecting region 112. The radiation rays emitted from the detecting region 112 may be used to generate CT data (also referred to as CT imaging information). The one or more detectors used in CT scan may include a scintillation detector (e.g., a cesium iodide detector), a gas detector, etc.

To prepare for a PET scan, a radionuclide (also referred to as "PET tracer" or "PET tracer molecules") may be introduced into the subject. The PET tracer may emit positrons in the detecting region 112 when it decays. An annihilation (also referred to as "annihilation event" or "coincidence event") may occur when a positron collides with an electron. The annihilation may produce two gamma photons, which may travel in opposite directions. The line connecting the detector units that detecting the two gamma photons may be defined as a "line of response (LOR)." One or more detector set on the gantry 111 may detect the annihilation events (e.g., gamma photons) emitted from the detecting region 112. The annihilation events emitted from the detecting region 112 may be used to generate PET data (also referred to as PET imaging information). In some embodiments, the one or more detectors used in the PET scan may be different from detectors used in the CT scan. In some embodiments, the one or more detectors used in the PET scan may include a plurality of scintillator crystals and light sensors coupled to the scintillator crystals. The scintillator crystals, arranged in a matrix of any suitable size, may be impinged by the gamma rays. The scintillator crystals may be formed by any suitable material, such as bismuth germinate (BGO), Cerium-doped Lutetium Yttrium Orthosilicate (LYSO), or Gadolinium Oxyorthosilicate (GSO). The light sensors may be any suitable photo-detectors that sense or detect light or other electromagnetic energy. The light sensors may be Silicon Photomultipliers (SiPMs) or photomultiplier tubes (PMT). The light sensors may be coupled at an end of the scintillator crystals opposite a detector face. In various embodiments, the surfaces of the scintillator not being coupled to the light sensors may be covered by a reflective layer, such as Teflon, TiO2 load Epoxy, or a spectral reflector.

The processing device 120 may process data and/or information obtained and/or retrieve from the imaging scanner 110, the terminal(s) 140, the storage device 130 and/or other storage devices. For example, the processing device 120 may obtain PET imaging information, and identify one or more regions of interest (ROIs) based on the PET imaging information. As a further example, the processing device 120 may analyze characteristics of signals of the one or more ROIs, and generate a medical diagnostic report regarding the subject. In some embodiments, a medical diagnostic report may be transmitted to the terminal(s) 140 and displayed on one or more display devices in the terminal(s) 140. In some embodiments, the processing device 120 may be a single server or a server group. The server group may be centralized or distributed. In some embodiments, the processing device 120 may be local or remote. For example, the processing device 120 may access information and/or data stored in the imaging scanner 110, the terminal(s) 140, and/or the storage device 130 via the network 150. As another example, the processing device 120 may be directly connected with the imaging scanner 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented on a computing apparatus 200 having one or more components illustrated in FIG. 2 in the present disclosure.

The storage device 130 may store data and/or instructions. In some embodiments, the storage device 130 may store data obtained from the terminal(s) 140 and/or the processing device 120. For example, the storage device 130 may store images, videos, algorithms, texts, instructions, program codes, etc. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected with the network 150 to communicate with one or more components of the imaging report generation system 100 (e.g., the processing device 120, the terminal(s) 140, etc.). One or more components of the imaging report generation system 100 may access the data or instructions stored in the storage device 130 via the network 150. In some embodiments, the storage device 130 may be directly connected with or communicate with one or more components of the imaging report generation system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal(s) 140 may remotely operate the imaging scanner 110. In some embodiments, the terminal(s) 140 may operate the imaging scanner 110 via a wireless connection. In some embodiments, the terminal(s) 140 may receive information and/or instructions inputted by a user, and send the received information and/or instructions to the imaging scanner 110 or the processing device 120 via the network 150. In some embodiments, the terminal(s) 140 may receive data and/or information from the processing device 120. In some embodiments, the terminal(s) 140 may be part of the processing device 120. In some embodiments, the terminal(s) 140 may be omitted.

In some embodiments, the terminal(s) 140 may send and/or receive information for imaging report generation to the processing device 120 via a user interface. The user interface may be in the form of an application for imaging report generation implemented on the terminal(s) 140. The user interface implemented on the terminal(s) 140 may be configured to facilitate communication between a user and the processing device 120. In some embodiments, a user may input a request or an instruction via the user interface implemented on a terminal 140. The terminal(s) 140 may send the request or instruction to the processing device 120 for generating a diagnostic imaging report as described elsewhere in the present disclosure (e.g., FIG. 6 and the descriptions thereof). In some embodiments, the user may identify and/or select a lesion from one or more ROIs via the user interface. In some embodiments, the user interface may facilitate the presentation or display of information and/or data (e.g., a signal) relating to diagnostic imaging report generation received from the processing device 120. In some embodiments, the information and/or data may be further configured to cause the terminal(s) 140 to display a generated diagnostic imaging report to the user.

The network 150 may include any suitable network that can facilitate the exchange of information and/or data for the imaging report generation system 100. In some embodiments, one or more components of the imaging report generation system 100 (e.g., the imaging scanner 110, the terminal(s) 140, the processing device 120, or the storage device 130) may communicate information and/or data with one or more other components of the imaging report generation system 100 via the network 150. For example, the processing device 120 may obtain CT imaging information from the imaging scanner 110 via the network 150. As another example, the processing device 120 may obtain user instructions from the terminal(s) 140 via the network 150. In some embodiments, the network 150 may be any type of wired or wireless network, or a combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging report generation system 100 may be connected with the network 150 to exchange data and/or information.

It should be noted that the above description of the imaging report generation system 100 is merely provided for the purposes of illustration, not intended to limit the scope of the present disclosure. For persons having ordinary skills in the art, components contained in the imaging report generation system 100 may be combined or adjusted in various ways, or connected with other components as subsystems, and various variations and modifications may be conducted under the teaching of the present disclosure. However, those variations and modifications may not depart the spirit and scope of this disclosure. For example, the imaging scanner 110 may be a standalone device out of the imaging report generation system 100, and the imaging report generation system 100 may be connected to or in communication with the imaging scanner 110 via the network 150. All such modifications are within the protection scope of the present disclosure.

FIG. 2 is a schematic diagram illustrating hardware and/or software components of an exemplary computing apparatus 200 on which the processing device 120 may be implemented according to some embodiments of the present disclosure. As illustrated in FIG. 2, the computing apparatus 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the imaging scanner 110, the terminal(s) 140, the storage device 130, and/or any other component of the imaging report generation system 100. Specifically, the processor 210 may process imaging information obtained from the imaging scanner 110. For example, the processor 210 may generate a diagnostic imaging report based on the imaging information. In some embodiments, the diagnostic imaging report may be stored in the storage device 130, the storage 220, etc. In some embodiments, the diagnostic imaging report may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing apparatus 200. However, it should be noted that the computing apparatus 200 in the present disclosure may also include multiple processors. Thus operations and/or method steps that are performed by one processor as described in the present disclosure may also be jointly or separately performed by the multiple processors. For example, if in the present disclosure the processor of the computing apparatus 200 executes both operation A and operation B, it should be understood that operation A and operation B may also be performed by two or more different processors jointly or separately in the computing apparatus 200 (e.g., a first processor executes operation A and a second processor executes operation B, or the first and second processors jointly execute operations A and B).

The storage 220 may store data/information obtained from the imaging scanner 110, the terminal(s) 140, the storage device 130, or any other component of the imaging report generation system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for diagnostic imaging report generation.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the imaging scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
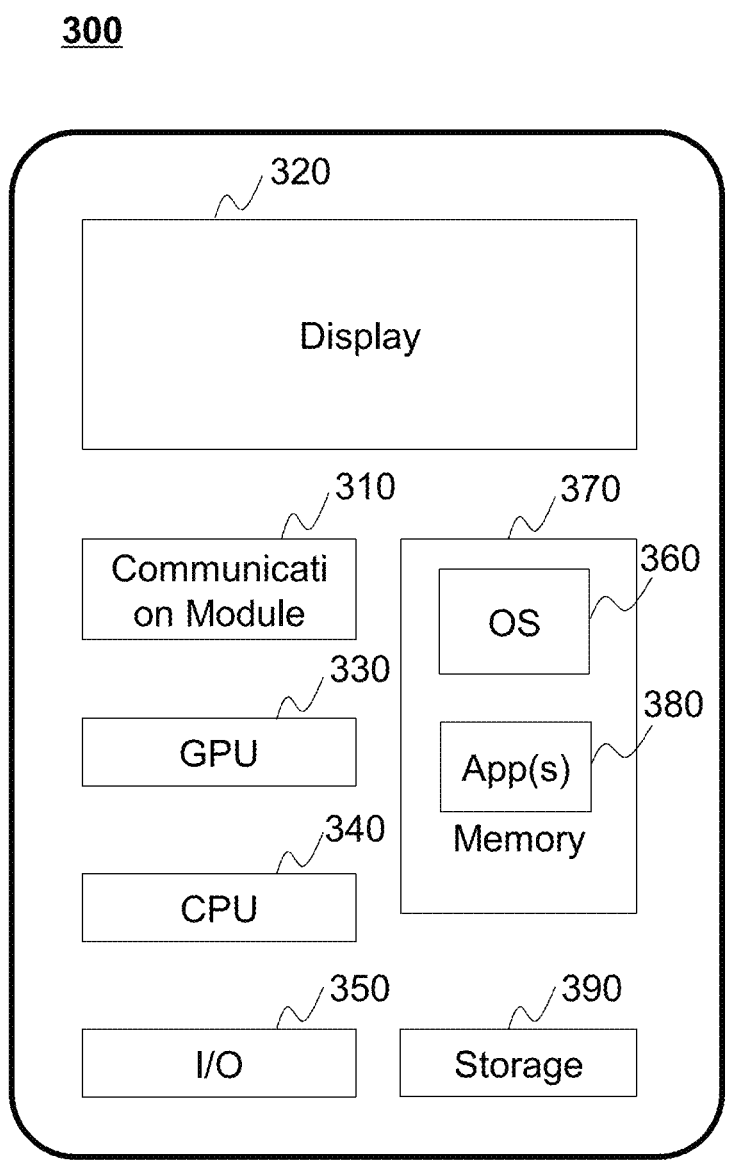
FIG. 3 is a schematic diagram illustrating hardware and/or software components of an exemplary mobile device 300 according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 370, and a storage 390. In some embodiments, any other suitable component, including but not limited to a system bus or a controller (not shown), may also be included in the mobile device 300. In some embodiments, a mobile operating system 360 (e.g., iOS, Android, Windows Phone, etc.) and one or more applications 380 may be loaded into the memory 370 from the storage 390 in order to be executed by the CPU 340. The applications 380 may include a browser or any other suitable mobile apps for receiving and rendering information relating to imaging information processing or other information from the processing device 120. User interactions with the information stream may be achieved via the I/O 350 and provided to the processing device 120 and/or other components of the imaging report generation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a diagnostic imaging report as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
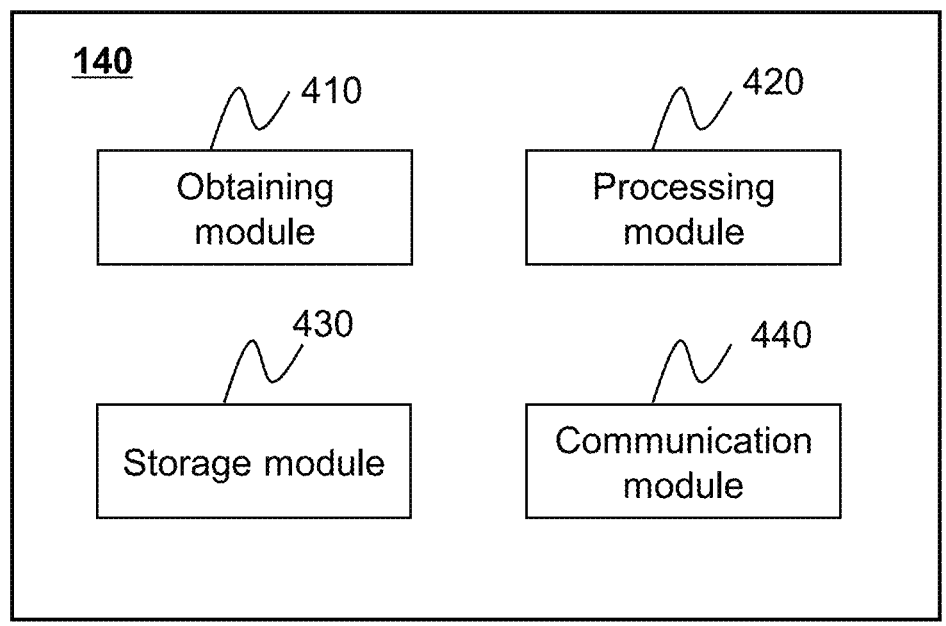
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may include an obtaining module 410, a processing module 420, an I/O module 430, and a communication module 440. One or more of the modules of the processing device 120 may be interconnected. The connection(s) may be wireless or wired. At least a portion of the processing device 120 may be implemented on a computing apparatus as illustrated in FIG. 2 or a mobile device as illustrated in FIG. 3.

The obtaining module 410 may obtain data and/or information. In some embodiments, the obtaining module 410 may obtain imaging information from a multi-modality imaging device. The imaging information may be acquired from a scan of a subject using the multi-modality imaging device. The imaging information may include an image (e.g., a two-dimensional (2D) image, a three-dimensional (3D) image, etc.), a video (e.g., a 2D video, a 3D video, etc.), image data (e.g., image data corresponding to an image or a video), or the like. The imaging information may be acquired from the imaging scanner 110, the storage device 130, or any other storage device as described elsewhere in the present disclosure.

The processing module 420 may process data and/or information, and generate a diagnostic imaging report based on the processed data. The processing module 420 may receive data and/or information from the obtaining module 410, the I/O module 430, and/or any storage devices capable of storing data (e.g., the storage device 130, or an external data source). In some embodiments, the processing module 420 may receive the imaging information from the obtaining module 410, and generate a diagnostic imaging report based on the imaging information.

The processing module 420 may include a hardware processor, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

The I/O module 430 may input or output signals, data or information. For example, the I/O module 430 may output a diagnostic imaging report to a user (e.g., a doctor, a patient, etc.). In some embodiments, the I/O module 430 may include an input device and an output device. Example input devices may include a keyboard, a mouse, a touch screen, a microphone, or the like, or a combination thereof. Example output devices may include a display device, a loudspeaker, a printer, a projector, or the like, or a combination thereof. Example display devices may include a liquid crystal display (LCD), a light-emitting diode (LED)-based display, a flat panel display, a curved screen, a television device, a cathode ray tube (CRT), or the like, or a combination thereof.

The communication module 440 may be connected to a network (e.g., the network 150) to facilitate data communications. The communication module 440 may establish connections between the processing device 120, the storage device 130, and/or the one or more terminals 140. For example, the communication module 440 may send a diagnostic imaging report to the one or more terminals 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G, etc.), or the like, or any combination thereof. In some embodiments, the communication module 440 may be and/or include a standardized communication port, such as RS232, RS485, etc. In some embodiments, the communication module 440 may be a specially designed communication port. For example, the communication module 440 may be designed in accordance with the digital imaging and communications in medicine (DICOM) protocol.

It should be noted that the above description of the processing device 120 is merely provided for the purpose of illustration, and not intended to limit the scope of the present disclosure. For persons having ordinary skills in the art, various variations and modifications may be performed in the light of the present disclosure. However, those variations and modifications do not depart from the scope of the present disclosure. For example, one or more of the modules of the processing device 120 mentioned above may be omitted or integrated into a single module. As another example, the processing device 120 may include one or more additional modules, for example, a storage module for data storage.

Figure 5:
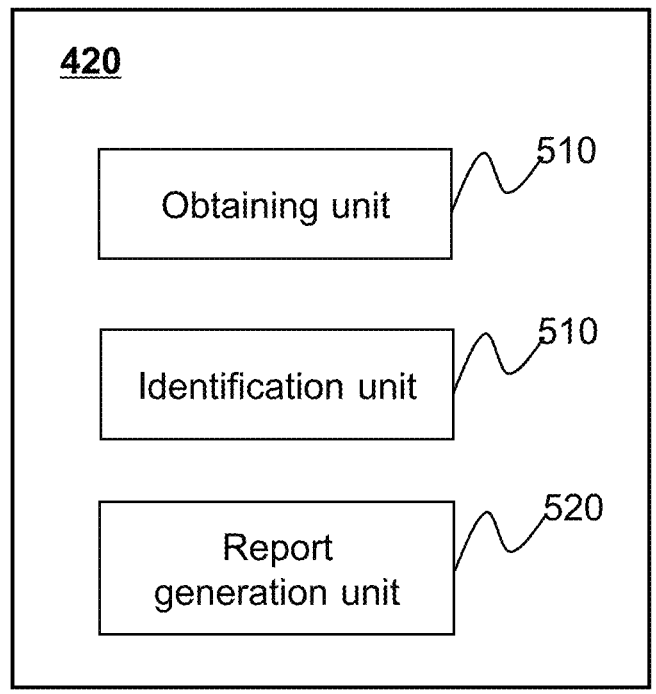
FIG. 5 is a block diagram illustrating an exemplary processing device according to some embodiments of the present disclosure.

FIG. 5 is a block diagram illustrating an exemplary processing device according to some embodiments of the present disclosure. The processing module 420 may include an obtaining unit 510, an identification unit 520, and a report generation unit 530.

The obtaining unit 510 may obtain first imaging information and second imaging information. The first imaging information may be acquired from an examination region of a subject using a first imaging device. The second imaging information may be acquired from the examination region of the subject using a second imaging device.

The identification unit 520 may identify one or more ROIs with respect to the first imaging information and/or the second imaging information. In some embodiments, the identification unit 520 may identify at least one first target ROI based on the first imaging information, and determine first reporting information corresponding to the at least one first target ROI. In some embodiments, the first reporting information may include at least one of an image, text, a video, or an annotation. In some embodiments, the identification unit 520 may identify at least two candidate ROIs based on the first imaging information and an image recognition technique. In some embodiments, the obtaining unit 510 may receive a region selection instruction from a user. The region selection instruction may direct the identification unit 520 to select at least one first target ROI from the at least two candidate ROIs. Exemplary image recognition techniques may include a scale-invariant feature transform (SIFT) technique, a speed up robust feature (SURF) technique, a features from accelerated segment test (FAST) technique, a binary robust independent elementary features (BRIEF) technique, an oriented FAST and rotated BRIEF (ORB) technique, a deep learning based recognition technique, or the like, or a combination thereof. In some embodiments, the identification unit 520 may identify a first target ROI based on first imaging information automatically using a first target ROI determination model.

In some embodiments, the identification unit 520 may identify at least one second target ROI with respect to the second imaging information based on the at least one first target ROI, and determine second reporting information corresponding to the at least one second target ROI. In some embodiments, the second reporting information may include at least one of an image, a video, text, an annotation, etc.

In some embodiments, the first imaging information and the second imaging information may be with respect to a same coordinate system. For example, the first imaging information the second imaging information are with respect to an anatomical coordinate system, which may be built according to the anatomy of the subject. The identification unit 520 may perform the image fusion or image registration between the first imaging information and the second imaging information according to the same coordinate system. After the image fusion or the image registration is performed, the identification unit 520 may identify at least one ROI associated with the at least one first target ROI in the second imaging information, and designate the identified at least one ROI associated with the at least one first target ROI as the at least one second target ROI.

The report generation unit 530 may generate a report based on at least a part of the first reporting information or the second reporting information. In some embodiments, the diagnostic imaging report may include at least one of an image, an annotation, text, or a video. In some embodiments, the annotation may be associated with an image or one or more video frames of a video. The annotation may include region features (e.g., the first region features and/or the second region features), such as a name, a length, an area, a density, a grayscale, or the like, or any combination thereof.

Figure 6:
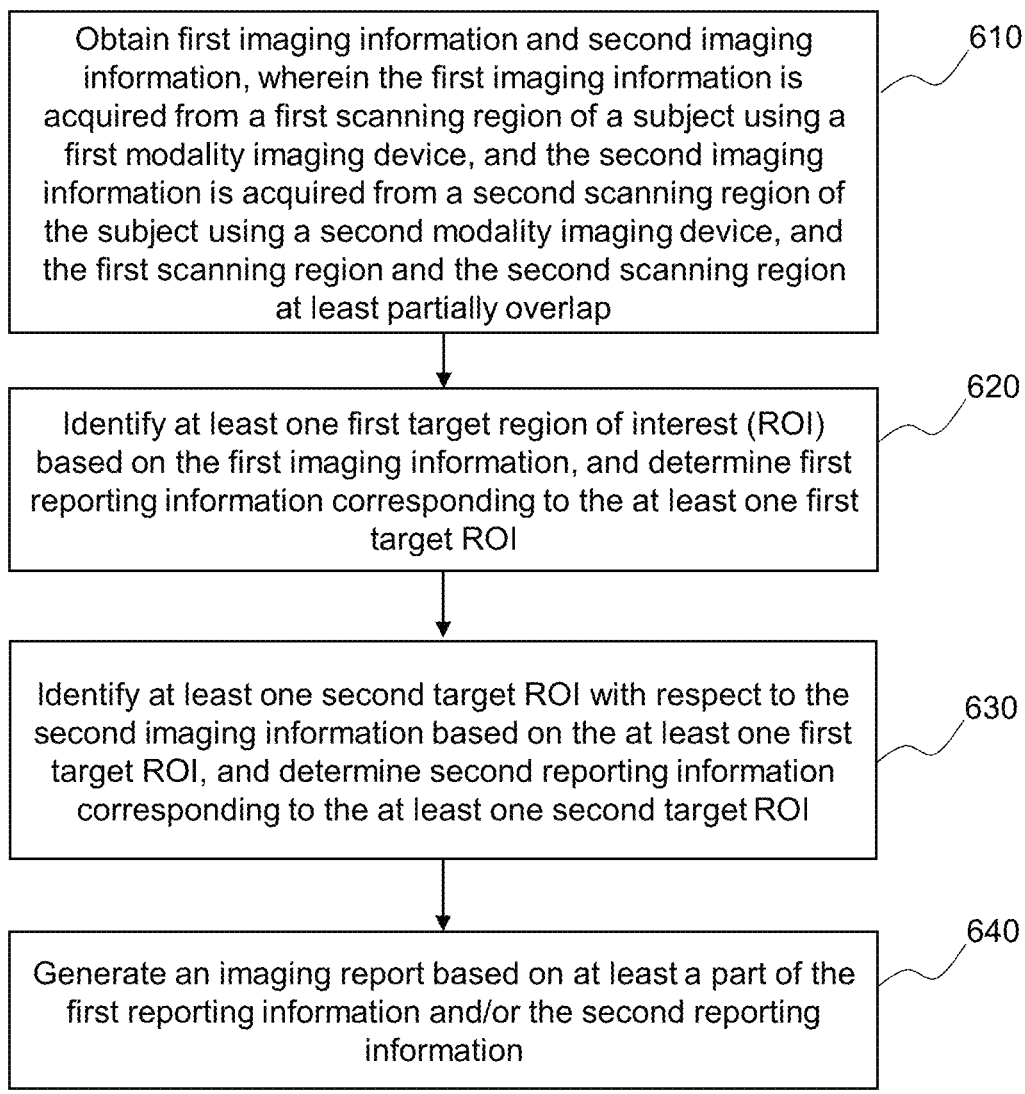
FIG. 6 is a flowchart of an exemplary process 600 for generating a diagnostic imaging report according to some embodiments of the present disclosure.

FIG. 6 is a flowchart illustrating an exemplary process 600 for generating a diagnostic imaging report according to some embodiments of the present disclosure. The process 600 may be executed by the processing device 120. For example, the process 600 may be implemented as a set of instructions (e.g., an application) stored in the storage, e.g., storage 220, the storage device 130, the storage 390, a storage device external to and accessible by the imaging report generation system 100. The processing device 120, the processor 210, and the CPU 340, may execute the set of instructions, and when executing the instructions, it may be configured to perform the process 600. The operations of the process 600 presented below are intended to be illustrative. In some embodiments, the process may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the obtaining module 410) may obtain first imaging information and second imaging information, wherein the first imaging information is acquired from an examination region of a subject using a first modality device, and the second imaging information is acquired from the examination region of the subject using a second modality device.

The first imaging information and/or the second imaging information may include an image (e.g., a 2D image, a 3D image, etc.), a video (e.g., a 2D video, a 3D video, etc.), or the like. In some embodiments, the first imaging information and/or the second imaging information may also include image data. The image data may be used to reconstruct an image or a video. For example, the second imaging information may include CT image data, which may be used to reconstruct a CT image. In some embodiments, the first imaging information and/or the second imaging information may further include raw data (i.e., original data acquired from an imaging scanner), processed data, a parameter used by the imaging scanner to acquire the raw data, etc.

In some embodiments, the first imaging information and the second imaging information may correspond to a same imaging phase. An imaging phase may relate to the state of a certain part of the subject at the time the image data is acquired by an imaging scanner. For example, an end of inhalation or exhalation of the subject may be deemed as an imaging phase. As another example, diastole of the heart of the subject may be deemed as an imaging phase. For instance, the first imaging information and the second imaging information may correspond to an end of inhalation of the subject.

In some embodiments, the first modality device may include a positron emission computed tomography (PET) scanner, a single photon emission computed tomography (SPECT) scanner, or the like, or any combination thereof. The first imaging information acquired using the first modality device may include molecular functional information of the examination region of the subject. Molecular functional information may correlate to physiological metabolism of one or more organs of the subject. The second modality device may include a magnetic resonance (MR) scanner, a computed tomography (CT) scanner, an optical scanner, an ultrasonic scanner, or the like, or any combination thereof. The second imaging information acquired using the second modality device may include anatomical information of the examination region of the subject. The anatomical information may correspond to a body structure of the subject. For example, the second imaging information acquired using an MR scanner may reflect a detailed structure of a kidney of the subject.

The first modality device may employ a first modality imaging technique to acquire the first imaging information. The second modality device may employ a second modality imaging technique to acquire the second imaging information. It is understood that the first modality imaging technique may be different from the second modality imaging technique so as to acquire imaging information of a certain region (e.g., the examination region) of the subject more comprehensively. Exemplary first modality imaging technique may include a time of flight (TOF)-PET reconstruction, a Monte Carlo simulation based reconstruction, a maximum likelihood estimation for Poisson model, a convolution back-projection technique, a filtered back-projection technique, a maximum posteriori reconstruction, etc.

Exemplary second modality imaging technique may include a compressed sensing based MR reconstruction, a half-Fourier imaging, a keyhole imaging, a parallel imaging, a back-projection technique, an iterative technique, a filtered back-projection technique, etc.

In some embodiments, the processing device 120 (e.g., the obtaining module 410) may obtain original imaging information of the examination region of the subject using the first modality device. In some embodiments, before the original imaging information is obtained, radionuclides such as carbon 11, fluorine 18, may be introduced into the subject. With the physiological metabolism of the subject, the introduced radionuclides may disperse in the whole body of the subject, thereby reflecting metabolic activities of tissues in the whole body of the subject. Imaging information obtained by scanning the tissues in the whole body of the subject using the first modality device may be defined as the original imaging information.

In some embodiments, the processing device 120 may determine the first imaging information based on the original imaging information. For example, processing device 120 may select a part of the original imaging information (e.g., the original imaging information in the examination region), and designate the selected part of the original imaging information as the first imaging information. In some embodiments, the processing device 120 (e.g., the obtaining module 410) may obtain an input of a user, and determine the first imaging information based on the original imaging formation and the input of the user. The user may provide input using a mouse, a keyboard, a touch screen, voice, a gesture, etc. In some embodiments, the input of the user may be an information selection operation. The information selection operation may be performed to select particular information from the original imaging information. For example, the obtaining module 410 may receive, for example, via the I/O module 430, an input of a doctor for selecting an upper part of the body of the subject. The processing device 120 may select the upper part of the body of the subject according to the input of the doctor, and designate original imaging information of the upper part of the body as the first imaging information.

In some embodiments, the first imaging information and/or the second imaging information may be in the form of an image, a video, an audio file, or the like, or a combination thereof. In some embodiments, the first imaging information and/or the second imaging information may be 3D images. In some embodiments, the first imaging information may be an image. The image may reflect a distribution of radionuclides. For example, pixels in a certain area of the image having higher gray values may indicate that the radionuclides may exist in a large quantity in a region of the body of the subject corresponding to the certain area of the image, and the region of the body of the subject may be diagnosed to be or include a malignant tumor with high metabolism. On the contrary, pixels in a certain area of the image having lower gray values may indicate that the radionuclides may exist in a small quantity in a region of the body of the subject corresponding to the certain area of the image, and the region of the body of the subject may be diagnosed to be or include healthy tissue.

In some embodiments, the second imaging information may be or include a set of 2D image sequences. A 2D image sequence may reflect anatomical information of a certain body part of the subject. The anatomical information may be used to determine a body structure of the subject. For example, the anatomical information may be used to identify an organ (e.g., a lung, a pelvic, etc.) of the subject through a contour of the organ.

In 620, the processing device 120 (e.g., the processing module 420) (e.g., the identification unit 510) may identify at least one first target ROI based on the first imaging information, and determine first reporting information corresponding to the at least one first target ROI. In some embodiments, the first reporting information may include at least one of an image, text, a video, or an annotation.

It is understood that one, two, or more than two first target ROIs may be identified based on the first imaging information. Radiation attenuation coefficients of different types of tissue may vary, thus resulting in different gray values between different types of tissue. In some embodiments, gray values of pixels in the at least one first target ROI may be different from gray values of pixels surrounding the at least one first target ROI. For example, gray values of pixels in the at least one first target ROI may be greater than gray values of pixels surrounding the at least one first target ROI.

In some embodiments, a region that satisfies a preset condition may be identified from the first imaging information using an image recognition algorithm. The identified region may be designated as a first target ROI. In some embodiments, the preset condition may relate to a range or threshold of gray values of pixels and/or a range or threshold of brightness values of pixels. For example, the preset condition may relate to a range of gray values of pixels from 150 to 255. If all pixels in a region have gray values greater than 150, the region may be designated as a first target ROI. In some embodiments, the preset condition may relate to a threshold value of a parameter or a range of values of the parameter. Merely by way of example, the parameter may be associated with a shape, an area, and/or a dimension of an anatomical structure in a region. The preset condition may be defined by a user, by the imaging report generation system 100 according to default settings of the imaging report generation system 100, etc.

In some embodiments, the processing device 120 (e.g., the identification unit 510) may identify at least two candidate ROIs based on the first imaging information and an image recognition technique. In some embodiments, the obtaining module 410 may receive a region selection instruction from a user. The region selection instruction may direct the processing module 420 to select at least one first target ROI from the at least two candidate ROIs.

Exemplary image recognition techniques may include a scale-invariant feature transform (SIFT) technique, a speed up robust feature (SURF) technique, a features from accelerated segment test (FAST) technique, a binary robust independent elementary features (BRIEF) technique, an oriented FAST and rotated BRIEF (ORB) technique, a deep learning based recognition technique, or the like, or a combination thereof.

In some embodiments, an image including the identified at least two candidate ROIs may be sent to a device for display (e.g., the display 320 of the mobile device 300). A user (e.g., a doctor) may review the image and select the at least one first target ROI from the identified at least two candidate ROIs in the image. The obtaining module 410 may receive a region selection instruction that corresponds to the selection operation of the user.

In some embodiments, the region selection operation of the user may be input into the processing device 120 using a mouse, a keyboard, a touch screen, a gesture, a piece of voice, or the like, or any combination thereof.

In some embodiments, the identification unit 510 may identify the at least one first target ROI based on the first imaging information and the image recognition technique automatically without the region selection instruction from the user. For example, the processing module 420 may identify the at least one first target ROI by inputting the first imaging information into a trained machine learning model, and the output of the trained machine learning model may be designated as the at least one first target ROI.

In some embodiments, each of the at least one first target ROI may correspond to a suspected lesion. A suspected lesion may be or include a malignant tumor with high metabolism. A user (e.g., a doctor) may determine whether a suspected lesion is a real lesion based on the first imaging information and/or the second imaging information.

After the at least one first target ROI is identified, the processing module 420 may determine first reporting information corresponding to the at least one first target ROI. In some embodiments, features of the at least one first target ROI may be determined. The features of the at least one first target ROI may also be referred to as first region features. In some embodiments, the first region features of each of the at least one first target ROI may include a range of gray values, a distribution of gray values, an area of a type of tissue, dimension of tissue in a certain direction, or the like, or any combination thereof.

For example, the processing module 420 may obtain gray values of pixels in a first target ROI, and determine the range of the gray values and the distribution of the gray values in the first target ROI. As another example, the processing module 420 may identify types of tissue in a first target ROI using, for example, a multi-threshold segmentation algorithm, and determine areas of the types of tissue, and/or dimensions in certain directions of the types of tissue.

In some embodiments, the processing module 420 may identify a first target ROI based on first imaging information automatically using a first target ROI determination model.

In some embodiments, a processing device, e.g., the processing device 120 or an external processing device (e.g., a processing device of a vendor who provides and/or maintains a such a model), may designate one or more regions in the at least two candidate ROIs other than the selected at least one first target ROI as filtered-out regions. The filtered-out regions and the at least one first target ROI may be used to train a preliminary model so as to generate a first target ROI determination model. Region selection operations of users may be used to train the first target ROI determination model. In some embodiments, the processing module 420 or the external processing device may determine characteristics of signals (e.g., signals received by the imaging scanner 110) of the filtered-out regions and the at least one first target ROI, and train the preliminary model based on the characteristics of signals related to the filtered-out regions and at least one first target ROI. The characteristics of signals of the filtered-out regions and the at least one first target ROI may be different in terms of at least one of a waveform, an amplitude, a frequency, a peak value, etc. The processing module 420 or the external processing device may obtain a plurality of set of historical data. A set of historical data may include one or more filtered-out regions and at least one first target ROI. In some embodiments, after a user performs a region selection operation, at least one first target ROI and one or more filtered-out regions may be determined, and the determined at least one first target ROI and the one or more filtered-out regions may be stored as a set of historical data.

The plurality of sets of historical data may be used to train the preliminary model so as to generate the first target ROI determination model.

The preliminary model may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a recurrent neural network (RNN) model, a convolutional network model, a hidden Markov model, a perceptron neural network model, a Hopfield network model, or the like, or any combination thereof. In some embodiments, the preliminary model may be a deep learning model.

In some embodiments, a deep learning algorithm may be used to train the deep learning model. Exemplary deep learning algorithms may include a neural network algorithm, a linear regression algorithm, a logistic regression algorithm, a decision tree algorithm, a SVM algorithm, a naive Bayes algorithm, a K nearest neighbor algorithm, a K-means algorithm, a random forest algorithm, a dimensionality reduction algorithm, a Gradient Boost algorithm, an Adaboost algorithm, etc.

In some embodiments, the training process of the preliminary model may also be referred to as an initialization process. The first target ROI determination model may be initialized using a large number (or count) of first target ROIs and filtered-out regions and/or based on knowledge of one or more users (e.g., users with rich experience).

Merely for illustration purposes, the processing module 420 may determine at least two candidate ROIs based on the first imaging information and an image recognition algorithm, and input the at least two candidate ROIs into the first target ROI determination model so as to obtain the at least one first target ROI. In some embodiments, the first target ROI determination model may be optimized, thereby improving the efficiency and/or accuracy of the detection of a first target ROI, reducing the need for user intervetion in the detection of a first target ROI, etc.

The processing module 420 may generate first reporting information corresponding to the at least one first target ROI based on the first region features of the at least one first target ROI. In some embodiments, the first reporting information may include at least one of an image, text, a video, or an annotation.

Merely for illustration purposes, the first reporting information may include at least a part of first imaging information of the at least one first target ROI, first region features of the at least one first target ROI (e.g., a range of gray values, a distribution of gray values, areas of certain types of tissue, dimensions of certain types of tissue, etc.), a location of each of the at least one first target ROI, techniques used to obtain the first imaging information, parameters of the first modality device used to scan the examination region, or the like, or any combination thereof.

In 630, the processing device 120 (e.g., the processing module 420) (e.g., the identification unit 510) may identify at least one second target ROI with respect to the second imaging information based on the at least one first target ROI, and determine second reporting information corresponding to the at least one second target ROI. In some embodiments, the second reporting information may include at least one of an image, a video, text, an annotation, etc.

It is understood that one, two, or more than two second target ROIs may be identified based on the second imaging information and the at least one first target ROI.

In some embodiments, both the first imaging information and the second imaging information may be 2D images or 3D images. The processing module 420 may perform an image fusion or an image registration between the first imaging information and the second imaging information so as to obtain at least one ROI in the second scanning information associated with the first target ROI, which may be designated as the at least one second target ROI. In some embodiments, a first target ROI and a corresponding second target ROI may correspond to a same area of the subject (i.e., a same part of the subject). In some embodiments, a first target ROI and a corresponding second target ROI may correspond to different areas of the subject (i.e., different parts of the subject). For example, the at least one second target ROI may be or include a region different from but associated with the first target ROI. The association between the at least one first target ROI and the corresponding second target ROI may be determined according to pathology or a correlation between anatomical structures. In some embodiments, a first target ROI and a corresponding second target ROI may overlap.

In some embodiments, the first imaging information and the second imaging information may be with respect to a same coordinate system. For example, the first imaging information the second imaging information are with respect to an anatomical coordinate system, which may be built according to the anatomy of the subject. The processing module 420 may perform the image fusion or image registration between the first imaging information and the second imaging information according to the same coordinate system. After the image fusion or the image registration is performed, the processing module 420 may identify at least one ROI associated with the at least one first target ROI in the second imaging information, and designate the identified at least one ROI associated with the at least one first target ROI as the at least one second target ROI.

The processing module 420 may generate second reporting information corresponding to the at least one second target ROI based on second region features of the at least one second target ROI. In some embodiments, the determination of the second region features may be the same as or similar to the determination of the first region features. For example, the second region features of each of the at least one second target ROI may include a range of gray values, a distribution of gray values, areas of tissues, lengths of tissues, or the like, or any combination thereof. Merely for illustration purposes, the second reporting information may include at least a part of second imaging information of the at least one second target ROI, second region features of the at least one first target ROI (e.g., a range of gray values, a distribution of gray values, areas of types of tissues, dimensions of types tissue in predetermined directions, etc.), a location of each of the at least one second target ROI, techniques used to obtain the second imaging information, parameters of the second modality device used to scan the examination region, or the like, or any combination thereof.

It should be noted that the forms of the first reporting information and the second reporting information may be the same or different. For example, the first reporting information may be reporting information in the form of an image, a video, or the like, and the second reporting information may be in the form of text. In some embodiments, the first reporting information may describe first features of the at least one first target ROI, and the second reporting information may describe second features of the at least one second target ROI so as to obtain a more comprehensive and rich imaging diagnostic report. The first features and the second features may be in the same or different dimensions (e.g., a size, a gray scale, etc.).

In 640, the processing device 120 (e.g., the processing module 420) (e.g., the report generation unit 520) may generate a diagnostic imaging report based on at least a part of the first reporting information and/or the second reporting information.

The diagnostic imaging report herein may also be referred to as a report, a medical diagnostic report, an imaging report, or a medical imaging report. It should be noted that the terms including report, imaging report, diagnostic imaging report, medical diagnostic report, or medical imaging report may be used interchangeably in the present disclosure.

In some embodiments, the diagnostic imaging report may include at least one of an image, an annotation, text, or a video. In some embodiments, the annotation may be associated with an image or one or more video frames of a video. The annotation may include region features (e.g., the first region features and/or the second region features), such as a name, a length, an area, a density, a grayscale, or the like, or any combination thereof.

In some embodiments, the report generation unit 520 may combine the first reporting information with the second reporting information to generate the diagnostic imaging report. In some embodiments, the report generation unit 520 may filter the first reporting information and/or the second reporting information according to a report filtering rule, and generate the diagnostic imaging report based on filtered first reporting information and/or filtered second reporting information. For example, the report generation unit 520 may filter second reporting information not including a second target ROI out, and generate the diagnostic imaging report based on first reporting information and filtered second reporting information. In some embodiments, the report generation unit 520 may correct the first reporting information according to the second reporting information, and generate the diagnostic imaging report according to the corrected first reporting information. For example, brown adipose tissue on the neck or the back of a patient may show a high concentration in a PET image, which may be diagnosed as a lesion (e.g., stored as at least a part of the first reporting information). If the brown adipose tissue shows a normal physiological concentration according to an MR image of a same anatomical position as the PET image, the brown adipose tissue may be disgnosed as normal tissue (e.g., stored as at least a part of the second reporting information). The first reporting information that the brown adipose tissue may be a lesion may be corrected according to the second reporting information that the brown adipose tissue may be normal tissue, and the diagnostic imaging report may be generated according to the corrected first reporting information. In some embodiments, the report generation unit 520 may correct the second reporting information according to the first reporting information, and generate the diagnostic imaging report according to the corrected second reporting information. For example, tissue at a position on the spine of a patient corresponding to an abnormal signal in an MR image may be diagnosed as having a hemangioma or endplate inflammation (e.g., stored as at least a part of the second reporting information). If the tissue shows an abnormally high concentration in an PET image, it may be diagnosed that bone metastases has occrred (e.g., stored as at least a part of the first reporting information). The second reporting information that the tissue may have a hemangioma or endplate inflammation may be corrected according to the first reporting information that bone metastatic has occurred in the tissue, and the diagnostic imaging report may be generated according to the corrected second reporting information.

According to some embodiments of the present disclosure, the first imaging information of the examination region may be acquired using the first modality device, and the second imaging information of the examination region may be acquired using the second modality device. More comprehensive information of a particular region in both the examination region and the examination region may be obtained by combining the first imaging information and the second imaging information. The first reporting information may be generated automatically according to the at least one first target ROI identified in the first imaging information. The second reporting information may be generated automatically. The second reporting information may relate to the at least one second target ROI corresponding to the at least one first target ROI. The diagnostic imaging report may be generated automatically by combining the first reporting information and the second reporting information. The diagnostic imaging report may present imaging information (e.g., images, videos, etc.) of the subject from multiple aspects and/or multiple dimensions. In this case, the diagnostic imaging report may be more comprehensive and rich. Compared to conventional techniques of generating diagnostic imaging reports, the systems and methods for generating an imaing report disclosure herein, may have a higher efficiency, lower operating costs, and need less intervention from operators.

Figure 7:
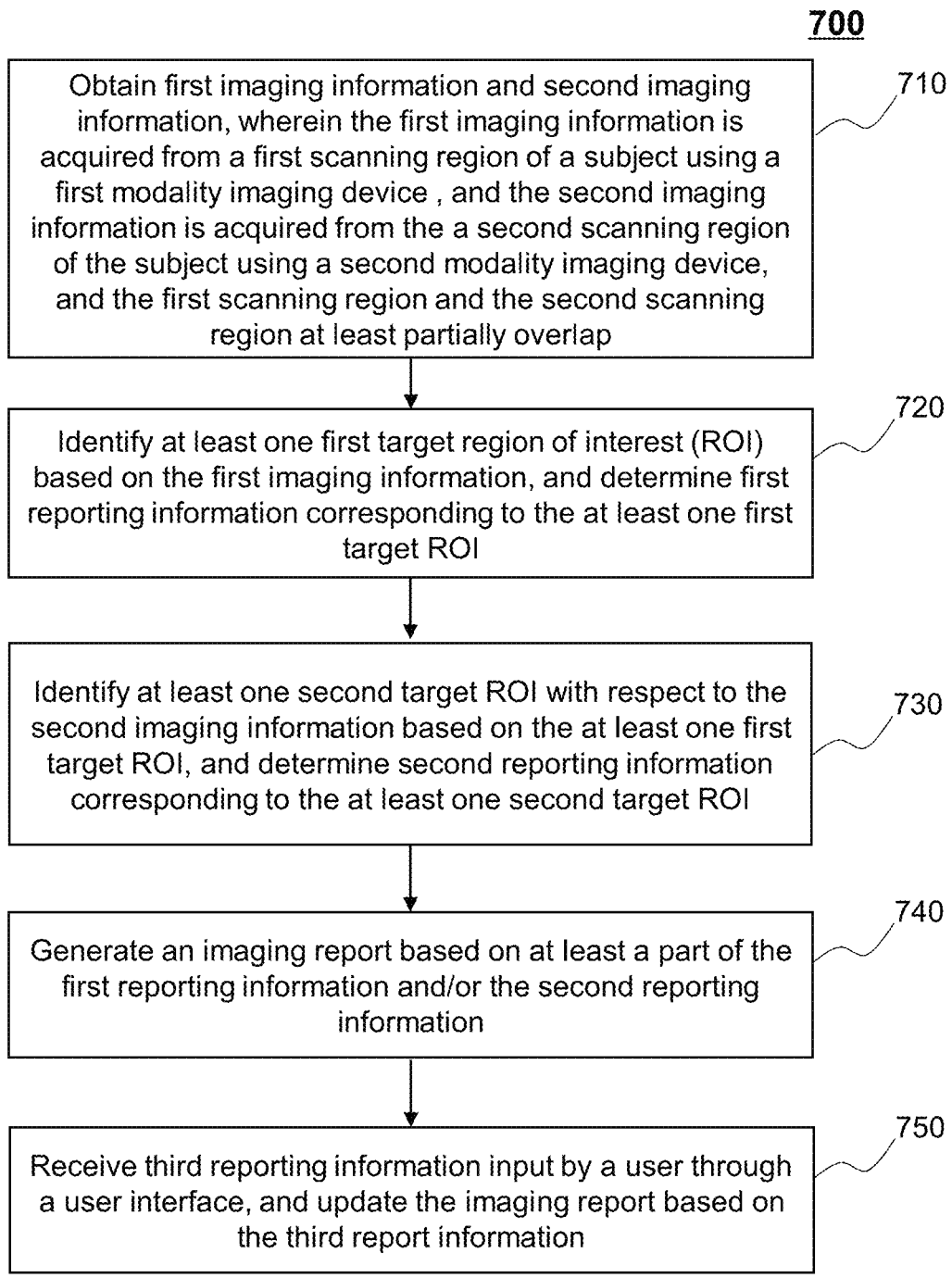
FIG. 7 is a flow chart of an exemplary process 700 for generating a diagnostic imaging report according to some embodiments of the present disclosure.

FIG. 7 is a flowchart of an exemplary process 700 for generating a diagnostic imaging report according to some embodiments of the present disclosure. The process 700 may be executed by the processing device 120. For example, the process 700 may be implemented as a set of instructions (e.g., an application) stored in the storage, e.g., storage 220, the storage device 130, the storage 390, a storage device external to and accessible by the imaging report generation system 100. The processing device 120, the processor 210, and the CPU 340, may execute the set of instructions, and when executing the instructions, it may be configured to perform the process 700. The operations of the process 700 presented below are intended to be illustrative. In some embodiments, the process may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 410) may obtain first imaging information and second imaging information, wherein the first imaging information is acquired from an examination region of a subject using a first modality device, and the second imaging information is acquired from the examination region of the subject using a second modality device.

In 720, the processing device 120 (e.g., the processing module 420) may identify at least one first target ROI based on the first imaging information, and determine first reporting information corresponding to the at least one first target ROI.

In 730, the processing device 120 (e.g., the processing module 420) may identify at least one second target ROI with respect to the second imaging information based on the at least one first target ROI, and determining second reporting information corresponding to the at least one second target ROI.

In 740, the processing device 120 (e.g., the processing module 420) may generate a diagnostic imaging report based on at least a part of the first reporting information and/or the second reporting information.

In some embodiments, the operations 710 through 740 may be similar to or the same as the operations 610 through 640 of the process 600 as illustrated in FIG. 6.

In 750, the processing device 120 (e.g., the processing module 420) may receive third reporting information input by a user through a user interface, and update the diagnostic imaging report based on the third report information.

In some embodiments, the third reporting information may include text, a mark, an image, a video, a table, or the like, or a combination thereof.

For example, the third reporting information may include text a user inputs through the I/O module 430. The text may include, e.g., descriptions of a suspected lesion. The text may be attached to an image of the suspected lesion or shown at a certain location of a reporting interface (e.g., the reporting interface 1300). As another example, the third reporting information may include a mark a user makes on a suspected lesion, for example, by drawing a circle enclosing a target ROI through the I/O module 430. As still another example, the third reporting information may include an image or a video of normal tissue a user causes to show so that the user may conveniently compare an image or a video of a suspected lesion with the image or video of normal tissue through the I/O module 430. As a further example, the third reporting information may include contents a user may provides through the I/O module 430. The contents may be arranged in the form of, e.g., a table. The contents may relate to one or more target ROIs, e.g., including suspected lesions. Exemplary contents may include descriptions of the suspected lesions, a diagnosis conclusion, etc.,. Such contents the user provides may be determined as third reporting information.

The third reporting information may be input by the user in a user interface of one or more terminals 140. For example, the third reporting information may be input through the I/O 350 implemented on the mobile device 300. In some embodiments, the third reporting information may be input, in an editable region where a description of the suspected lesions may be provided, through a keyboard, a touch screen, a mouse, a voice input, etc. In some embodiments, the third reporting information may be selected from multiple options describing features of one or more suspected lesions using a mouse, a touch screen, etc. Merely by way of example, the user may select one or more options describing certain lesions in a drop-down list according to, for example, the first imaging report and/or the second imaging report.

In some embodiments, the imaging report generated in 740 may be updated according to the third reporting information. In some embodiments, the diagnostic imaging report may be updated by content modification, replacement, and/or supplementation according to the third reporting information. For instance, the diagnostic imaging report may be updated by modifying at least a part of the imaging report generated in 740 according to the third reporting information, replacing at least a part of contents of the imaging report generated in 740 by the third reporting information, adding the third reporting information to the diagnostic imaging report generated in 740, or the like, or any combination thereof.

In some embodiments, the third reporting information may be an optional part of the diagnostic imaging report. In other words, in some embodiments, operation 750 may be omitted. In some embodiments, the operations for updating the diagnostic imaging report according to the third reporting information in 750 may be incorporated into 740. In other words, the diagnostic imaging report may be generated based on the first reporting information, the second reporting information, and the third reporting information.

According to some embodiments of the present disclosure, a more accurate, complete, and readable diagnostic imaging report may be produced by content modification, replacement, and/or supplementation according to the third reporting information on the basis of the first reporting information and the second reporting information. By updating the imaging report generated in 740 according to the third reporting information, the diagnostic imaging report may be more accurate, rich, and comprehensive, and technical problems that conventional imaging diagnostic reports are hard to read by doctors and patients may be solved, thus providing more scientific and comprehensive imaging diagnostic reports, improving the accuracy, as well as the readability of diagnostic imaging reports.

Figure 8:
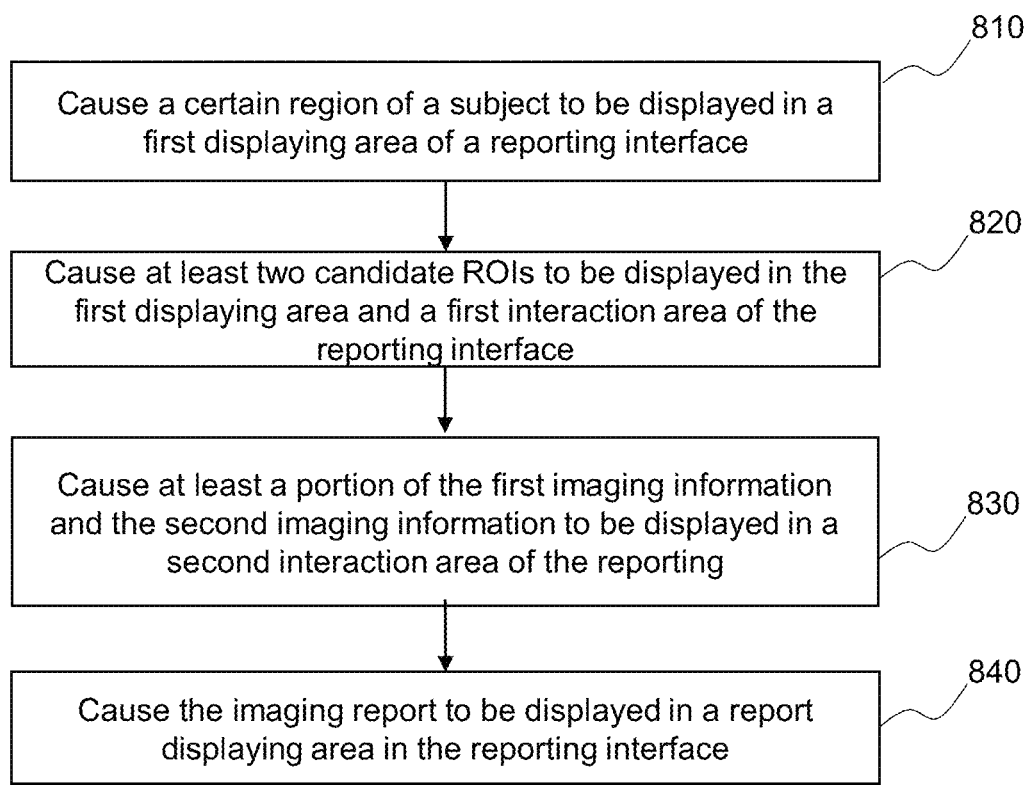
FIG. 8 is a flow chart illustrating an exemplary process for causing a diagnostic imaging report to be displayed in a report displaying area in the reporting interface according to some embodiments of the present disclosure.

FIG. 8 is a flowchart illustrating an exemplary process for causing a diagnostic imaging report to be displayed in a report displaying area in the reporting interface according to some embodiments of the present disclosure. The operations of the process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 120 may cause an image repsenting a certain region of a subject to be displayed in a first displaying area of a reporting interface. In some embodiments, the reporting interface may be implemented on the one or more terminals 140 of the imaging report generation system 100. For example, the reporting interface may be a user interface of the mobile device 300 through which a doctor may review and/or edit a diagnostic imaging report of a subject. The user interface may be displayed in the display 320. The reporting interface may include an interaction area and a displaying area. The displaying area may include a first displaying area and a report displaying area. The interaction area may include a first interaction area and a second interaction area. The first interaction area, the second interaction area, the first displaying area, and the report displaying area may be arranged at different positions in the reporting interface. More descriptions regarding the configuration of the reporting interface may be found elsewhere in the present disclosure. See, for example, FIG. 13 and the descriptions thereof.

The first displaying area may display first imaging information of the subject. After the first imaging information is acquired using the first modality device, the first imaging information of the subject may be displayed in the first displaying area in the reporting interface. In some embodiments, the first imaging information may include at least one image, such as a PET image, a SPECT image, etc. The at least one image may include a portion representing a certain region of the subject. In some embodiments, the certain region shown in the at least one image may relate to the examination region. For example, if the first modality device scans the entire body of the subject (i.e., the examination region is the entire body of the subject), the certain region shown in the at least one image may include the entire body or a portion of the entire body of the subject. As another example, if the first modality device scans an upper part of the body of the subject (i.e., the examination region is the upper part of the body of the subject), the certain region shown in the at least one image may include the upper part of the body or a portion of the upper part of the subject.

In 820, the processing device 120 may cause at least two candidate ROIs to be displayed in the first displaying area and a first interaction area of the reporting interface. The at least two candidate ROIs may be identified based on the first imaging information. In some embodiments, the at least two candidate ROIs may be identified according to pixels of the at least one image using an image recognition technique, such as a scale-invariant feature transform (SIFT) technique, a speed up robust feature (SURF) technique, a features from accelerated segment test (FAST) technique, a binary robust independent elementary features (BRIEF) technique, an oriented FAST and rotated BRIEF (ORB) technique, a deep learning based recognition technique, etc. Merely by way of example, pixels in a certain portion of the at least one image having higher gray values may indicate that there is a larger quantity of radionuclides in the region of the body of the subject corresponding to the certain region of the at least one image, and the region of the body of the subject may be diagnosed to be or include one or more suspected lesions with high metabolism. In some embodiments, the at least two candidate ROIs may be shown in the certain portion of the at least one image representing the region of the subject displayed in the first displaying area. For example, contours of the at least two candidate ROIs may be determined so as to distinguish the at least two candidate ROIs from pixels surrounding the at least two candidate ROIs. The contours of the at least two candidate ROIs may be represented in the form of dashed lines, dotted lines, bold lines, etc.

In some embodiments, a plurality of region identifications (e.g., region selection icons) corresponding to the at least two candidate ROIs in the at least one image may be arranged in the first interaction area. A user (e.g., a physician) may select at least one first target ROI from the at least two candidate ROIs. For instance, a list of icons each of which corresponds to one of the at least two candidate target ROIs may be shown in the first interaction area; the user may select any one of the at least two candidate ROIs by clicking on its corresponding icon. The at least one first target ROI may be determined as at least one suspected lesion. The user may determine whether each of the at least one suspected lesion is a real lesion based on the first imaging information and/or the second imaging information. In some embodiments, the selected candidate ROI(s) may be highlighted to convey the user selection. For instance, when the user selects, from the list of icons in the first interaction area, an icon which corresponds to a suspected lesion, a contour of the suspected lesion may be highlighted, for example, in a particular color, in the at least one image in the first displaying area simultaneously.

In some embodiments, the first interaction area may at least partially overlap the first displaying area. The at least two candidate ROIs may be shown differently so as to be distinguishable. For instance, the at least two candidate ROIs may be shown as regions filled with different colors. As another example, the contours of the at least two candidate ROIs may be shown so that they are visually distingushable. A candidate ROI may be clickable for selection. The user may select any one of the at least two candidate ROIs by, e.g., clicking on it. A selected candidate ROI may be marked to show its status as being selected.

In 830, the processing device 120 may cause at least a portion of the first imaging information and the second imaging information to be displayed in a second interaction area of the reporting interface. In some embodiments, when the user selects an icon in the first interaction area, at least a portion of first imaging information (e.g., PET images) of a suspected lesion corresponding to the icon second imaging information (e.g., MR images) of the suspected lesion may be displayed in the second interaction area. Additionally or alternatively, fused imaging information of the suspected lesion (e.g., a fused image of the PET image(s) and the MR image(s)) may be displayed in the second interaction area.

In some embodiments, the second interaction area may include two or more sub-areas. The first imaging information of the suspected lesion, the second imaging information of the suspected lesion, and/or the fused imaging information of the suspected lesion may be displayed in the two or more sub-areas of the second interaction area. Merely for illustration purposes, the first imaging information including a first plurality of PET images of the suspected lesion may be displayed in one or more rows in a first sub-area of the second interaction area, and the second imaging information including a second plurality of MR images of the suspected lesion may be displayed, in one or more rows, in a second sub-area of the second interaction area. The first plurality of PET images and the second plurality of MR images may be displayed in different scales, which may be set by a user, according to default settings of the imaging report generation system 100, etc. In some embodiments, the user may change the position of the first plurality of PET images and/or the second plurality of MR images in the first sub-area and the second sub-area. For example, a doctor may adjust a position of an MR image from an end position of a second row to a start position of a first row in the second sub-area since the MR image provides a significant characteristic of the suspected lesion. In some embodiments, the user may delete one or more images from the first plurality of PET images and/or the second plurality of MR images. It should be noted that the user may make various adjustments or modifications to the first imaging information, the second imaging information, and/or the fused imaging information displayed in the second interaction area.

In 840, the processing device 120 may cause the diagnostic imaging report to be displayed in a report displaying area in the reporting interface. In some embodiments, the diagnostic imaging report may include at least a part of the first reporting information, the second reporting information, and/or the third reporting information. In some embodiments, the diagnostic imaging report may include at least one of an image, a video, text, or an annotation. For example, the diagnostic imaging report may include information in the form of text including items such as characteristics of signals of one or more suspected lesions, locations of lesions, an imaging technique used, descriptions of lesions, a diagnosis conclusion, etc. In some embodiments, the descriptions of lesions and/or the diagnosis conclusion may be input or edited by the user through the I/O module 430. For example, third imaging information of a suspected lesion, which is input by a doctor based on first imaging information and/or second imaging information of the suspected lesion, may be added into the descriptions of lesions of the report displaying area.

Figure 9:
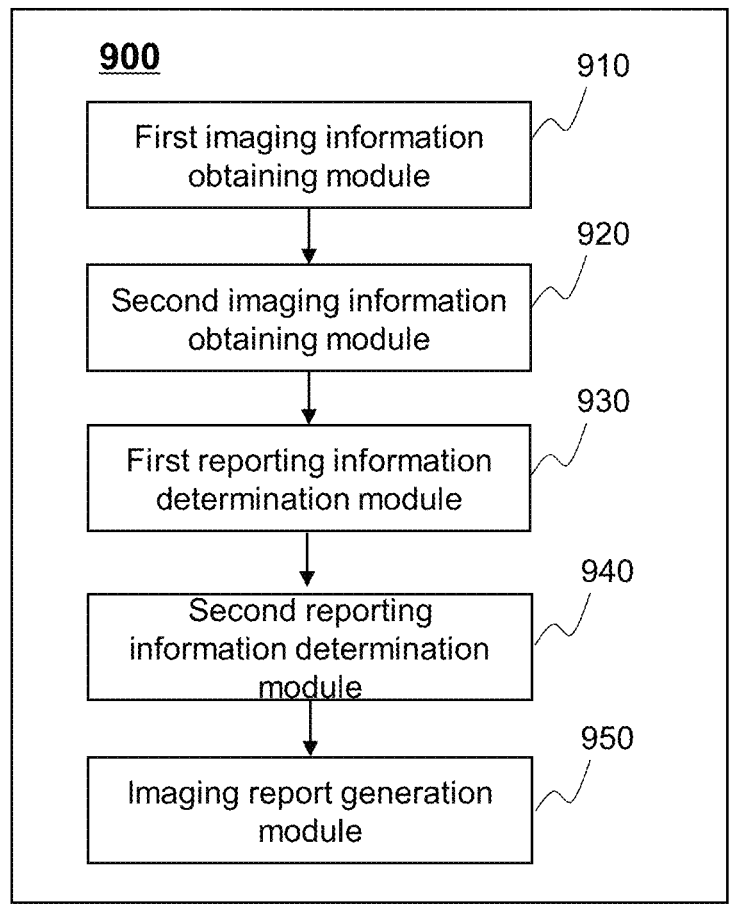
FIG. 9 is a block diagram of a processing device for generating a diagnostic imaging report according to some embodiments of the present disclosure.

FIG. 9 is a block diagram of a processing device for generating a diagnostic imaging report according to some embodiments of the present disclosure. As shown in FIG. 9, the processing device 900 may include a first imaging information obtaining module 910, a second imaging information obtaining module 920, a first reporting information determination module 930, a second reporting information determination module 940, and an imaging report generation module 950. One or more of the modules of the processing device 900 may be interconnected. The connection(s) may be wireless or wired. At least a portion of the processing device 900 may be implemented on a computing apparatus as illustrated in FIG. 2 or a mobile device as illustrated in FIG. 3.

The first imaging information obtaining module 910 may obtain first imaging information from an examination region of a subject using a first modality device. The second imaging information obtaining module 920 may obtain second imaging information from the examination region of the subject using a second modality device. The first reporting information determination module 930 may identify at least one first target ROI based on the first imaging information, and determine first reporting information corresponding to the at least one first target ROI. The second reporting information determination module 940 may identify at least one second target ROI with respect to the second imaging information based on the at least one first target ROI, and determine second reporting information corresponding to the at least one second target ROI. The image reporting information generation module 950 may generate a diagnostic imaging report based on at least a part of the first reporting information and/or the second reporting information.

According to some embodiments of the present disclosure, the first imaging information of the examination region may be acquired using the first modality device, and the second imaging information of the examination region may be acquired using the second modality device. More comprehensive information of a particular region in both the examination region and the examination region may be obtained by combining the first imaging information and the second imaging information. The first reporting information may be generated automatically according to the at least one first target ROI identified in the first imaging information. The second reporting information may be generated automatically. The second reporting information may relate to the at least one second target ROI corresponding to the at least one first target ROI. The diagnostic imaging report may be generated automatically by combining the first reporting information and the second reporting information. The diagnostic imaging report may present imaging information (e.g., images, videos, etc.) of the subject from multiple aspects and/or multiple dimensions. In this case, the diagnostic imaging report may be more comprehensive and rich. Compared to conventional techniques of generating diagnostic imaging reports, the systems and methods for generating an imaging report disclosure herein, may have a higher efficiency, lower operating costs, and need less intervention from operators.

In some embodiments, the first imaging information obtaining module 910 may be configured to obtain the first imaging information from the examination region of the subject using a PET scanner or a SPECT scanner.

In some embodiments, the first imaging information obtaining module 910 may further include an original imaging information acquisition unit and a first imaging information determination unit (not shown in the figure). The original imaging information acquisition unit may be configured to acquire original imaging information of a preset scanning region (e.g., the examination region) of the subject using the first modality device. The first imaging information determination unit may be configured to determine the first imaging information from the original imaging information according to a selection operation or filtering rule received from the user.

In some embodiments, the second imaging information obtaining module 920 may be further configured to obtain the second imaging information from the examination region of the subject using a MR scanner, a CT scanner, an optical scanner, an ultrasonic scanner, or the like.

In some embodiments, the first reporting information determination module 930 may further include a candidate ROI determination unit, a selection operation receiving uni, a first target ROI determination unit, and a first reporting information determination unit (not shown in the figure). The candidate ROI determination unit may be configured to determine at least two candidate ROIs based on the first imaging information and an image recognition technique. The selection operation receiving unit may be configured to receive a region selection operation input by the user. The first target ROI determination unit may be configured to determine at least one first target ROI from the at least two candidate ROIs according to the region selection operation input by the user. The first reporting information determination unit may be configured to determine the first reporting information corresponding to the at least one first target ROI.

In some embodiments, the first reporting information determination module 930 may further include a first target ROI determination model acquisition unit. The first target ROI determination model acquisition unit may be configured to designate one or more regions in the at least two candidate ROIs other than the selected at least one first target ROI as filtered-out regions; and generate a first target ROI determination model by training a preliminary model (e.g., deep learning model) based on the filtered-out regions and at least one first target ROI.

In some embodiments, the first target ROI determination unit may further be configured to input the at least two candidate ROIs into the first target ROI determination model to obtain the at least one first target ROI.

In some embodiments, the processing device 900 may further include a report updating module (not shown in the figure). The report updating module may be configured to receive third reporting information input by the user in a preset user interface, and update the report according to the third reporting information.

The device for generating diagnosis reports provided by the embodiments of the present disclosure may execute one or more methods for generating diagnosis reports provided by, for example, in the embodiments in FIGS. 6 through 8 of the present disclosure so as to achieve the beneficial effects described above.

Figure 10:
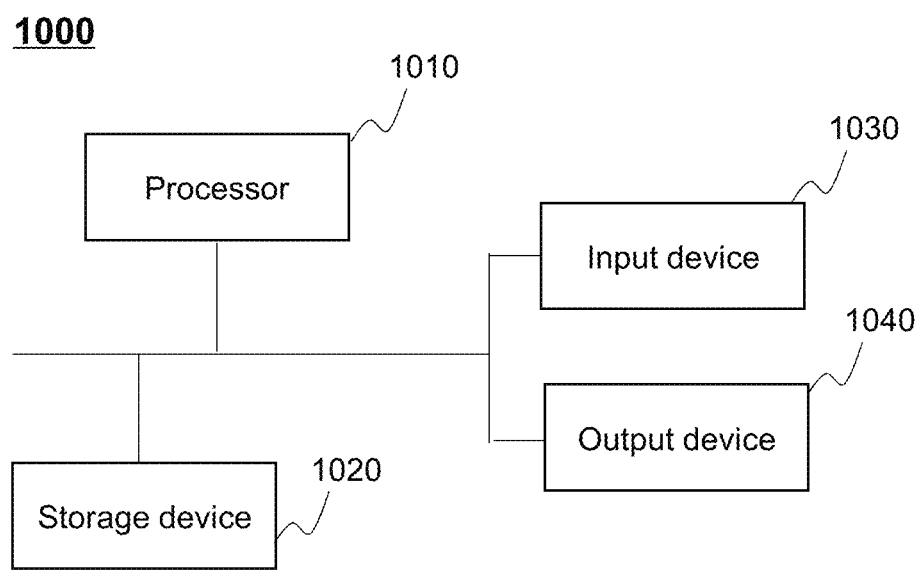
FIG. 10 is a schematic diagram of a processing device according to some embodiments of the present disclosure.

FIG. 10 is a schematic diagram of a processing device according to some embodiments of the present disclosure. As shown in FIG. 10, the processing device 1000 may include a processor 1010, a storage device 1020, an input device 1030, and an output device 1040. Only one processor 1010 is described in the processing device 1000. However, it should be noted that the processing device 1000 in the present disclosure may also include multiple processors. The processor 1010, the storage device 1020, the input device 1030, and the output device 1040 in the processing device 1000 may be connected via a bus or other connecting means.

The storage device 1020 may be a computer readable storage medium used to store software programs, computer executable programs, and one or more of the modules described above. For example, the storage device 1020 may store program instructions or modules (e.g., the first imaging information obtaining module 910, the second imaging information obtaining module 920, the first reporting information determination module 930, the second reporting information determination module 940, and/or the imaging report generation module 350) for generating diagnostic imaging reports in the present disclosure embodiment. The processor 1010 may run various applications and process multimedia information by executing the software programs, instructions, and modules stored in the storage device 1020 so as to generate a diagnostic imaging report.

In some embodiments, the storage device 1020 may include a program storage area and a multimedia information storage area. The program storage area may store an operating system and at least one application. The multimedia information storage area may store multimedia information created by, for example, the imaging scanner 110, one or more terminals 140, etc. In addition, the storage device 1020 may include a high speed random access memory, a non-volatile memory, such as a magnetic disk storage device, a flash memory device, or other non-volatile solid state storage devices. In some embodiments, the storage device 1020 may further include a memory located remotely relative to the processor 1010, which may connect to the processing device 1000 via a network. Exemplary network connection may include but not limited to, an Internet, an intranet, a local area network, a mobile communication network, or the like, or any combination thereof.

The input device 1030 may be used to receive an input (e.g., numbers, characters, etc.) from a user, and generate signals related to user settings and/or function control of the processing device 1000. The output device 1040 may include a display device, such as a display screen, a printer, etc.

Example input devices may include a keyboard, a mouse, a touch screen, a microphone, or the like, or a combination thereof. Example output devices may include a display device, a loudspeaker, a printer, a projector, or the like, or a combination thereof. Example display devices may include a liquid crystal display (LCD), a light-emitting diode (LED)-based display, a flat panel display, a curved screen, a television device, a cathode ray tube (CRT), or the like, or a combination thereof.

Figure 11:
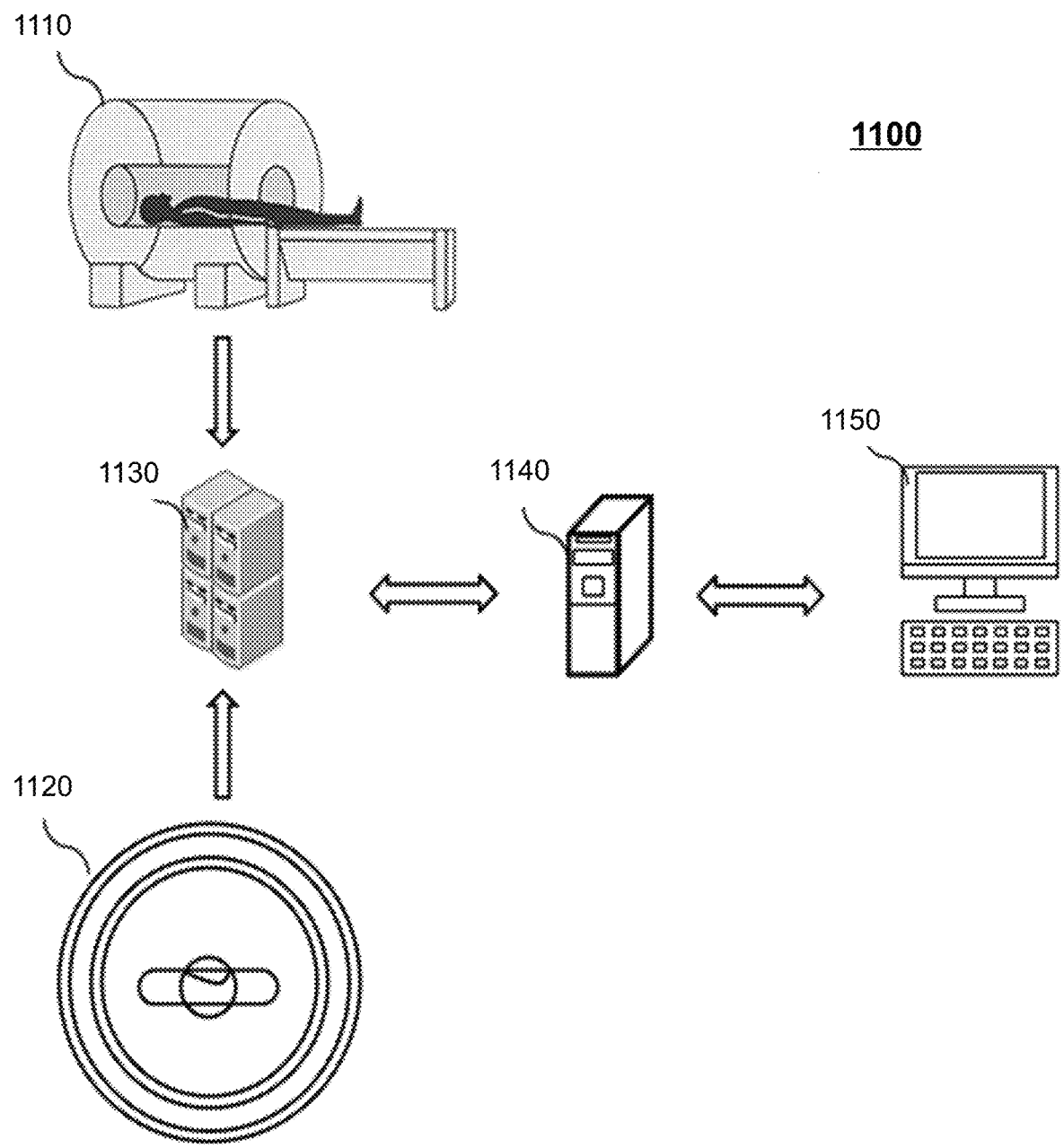
FIG. 11 is a schematic diagram of an imaging report generation device according to some embodiments of the present disclosure.

FIG. 11 is a schematic diagram of an imaging report generation device according to some embodiments of the present disclosure. For illustration purposes, the imaging report generation device 1100 may generate a PET-MR imaging report using a multi-modality scanner (e.g., a PET-MR scanner). As shown in FIG. 11, the imaging report generation device 1100 may include an MR scanner 1110, a PET scanner 1120, an imaging processor 1130, a controller 1140, and a display 1150.

The MR scanner 1110 may acquire MR imaging data of the examination region in an imaging scan, and reconstruct an MR image based on the MR imaging data. The PET scanner 1120 may acquire PET imaging data of the examination region in an imaging scan, and reconstruct a PET image based on the PET imaging data. In some embodiments, the MR scanner 1110 and the PET scanner 1120 may be integrated into a multi-modality imaging apparatus. The MR imaging data and the PET imaging data may be acquired simultaneously or sequentially. In some embodiments, the MR imaging data and/or the PET imaging data may be stored in a storage medium such as a hard disk or a cloud memory, and may be retrieved from the storage medium when the imaging report generation device 1100 needs to reconstruct MR images and/or and PET images.

The imaging processor 1130 may obtain the first imaging information of the examination region of the subject acquired using the first modality device, obtain the second imaging information of the examination region of the subject acquired using the second modality device, determine the at least one first target ROI based on the first imaging information, determine the at least one second target ROI in the second imaging information based on the at least one first target ROI, and generate the diagnostic imaging report based on the at least one first target ROI and the at least one second target ROI. In combination with the multi-modality imaging apparatus as illustrated in FIG. 11, the first modality device may be the PET scanner 1120 and the second modality device may be the MR scanner 1110, the first imaging information may be PET images and/or PET imaging data, and the second imaging information may be MR images and/or MR imaging data. The imaging processor 1130 may reconstruct the MR imaging data to generate MR images of the at least one first target ROI, and/or reconstruct the PET imaging data to generate PET images of the at least one second target ROI. In some embodiments, the PET images may be corrected using attenuation maps. In some embodiments, the attenuation maps may be obtained by scanning the subject using a CT scanner.

In some embodiments, the imaging processor 1130 may perform an image registration between the MR images and PET images so as to obtain correspondence relationships between the MR images and PET images. For example, the imaging processor 1130 may register an MR image with a PET image or register a PET image to an MR image. Exemplary image registration techniques may include an optical flow field technique, a feature point based registration technique, a contour based registration technique, a gray level based registration technique, or the like.

In some embodiments, the imaging processor 1130 may be local or remote relative to the MR scanner 1110 and/or the PET scanner 1120. The MR scanner 1110 and the PET scanner 1120 may share the imaging processor 1130 or use different image processors.

The controller 1140 may monitor or control the MR scanner 1110, the PET scanner 1120, the imaging processor 1130, and/or the display 1150. In some embodiments, the controller 1140 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), an ARM processor, or the like, or any combination thereof.

The display 1150 may display MR images of one or more ROIs, a PET image of one or more ROIs, fused images of one or more PET image and one or more MR images, etc. Further, the display 1150 may also display parameters such as height, weight, age, an imaging location of the subject, the MR scanner 1110, the operating state of the MR scanner 1110, the PET scanner 1120, the operating state of the PET scanner, or the like. In some embodiments, the display 1150 may be a cathode ray tube (CRT) display, a liquid crystal display (LCD), an organic light emitting display (OLED), a plasma display, or the like.

The imaging report generation device 1100 may connect to a network for facilitating data transmission. The network may include a local area network (LAN), a wide area network (WAN), a public network, a private network, a proprietary network, a public switched telephone network (PSTN), an Internet, a wireless network, a virtual network, or the like, or any combination thereof.

Figure 12A:
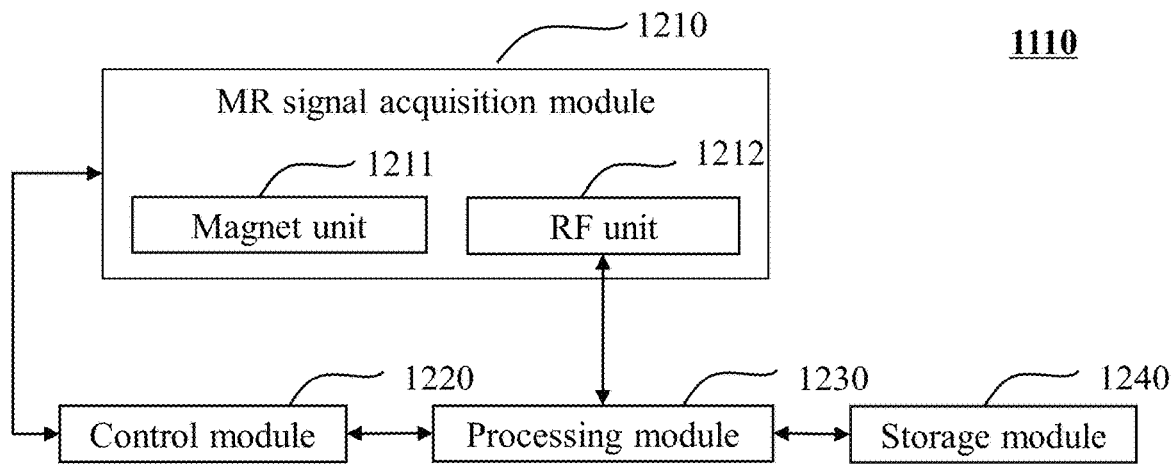
FIG. 12A is a block diagram of an MR scanner according to some embodiments of the present disclosure.

FIG. 12A is a block diagram of an MR scanner according to some embodiments of the present disclosure. The MR scanner 1110 may include an MR signal acquisition module 610, a control module 1220, and a processing module 1230, and a data storage module 1240. The MR signal acquisition module 1210 may include a magnet unit 1211 and a radio frequency (RF) unit 1212. The magnet unit 1211 may include a main magnet that generates a main magnetic field $B_0$ and gradient components that generate a gradient magnetic field. The main magnet may be a permanent magnet or a superconducting magnet, and the gradient components may include gradient current amplifiers and gradient coils. The gradient components may also include three independent channels $G_x$, $G_y$, $G_z$. Each gradient amplifier may excite one of the gradient coils, and generate a gradient field for producing spatial encoding signals so as to locate a magnetic resonance signal in a 2D or 3D space. The RF unit 1212 may include an RF transmitting coil and an RF receiving coil. The RF transmitting coil may transmit an RF pulse signal to a subject (e.g., a human body). The RF receiving coil may receive magnetic resonance signals from the human body. The RF coils of the RF unit 1212 may include body coils and local coils. In some embodiments, the body coils or local coils may be in various types, such as a birdcage coil, a solenoid coil, a saddle coil, a Helmholtz coil, an array coil, a loop coil, or the like. In some embodiments, the local coils may be arranged as an array coil, and the array coil may be set to a 4-channel mode, an 8-channel mode, or a 16-channel mode. The magnet unit 1211 and the RF unit 1212 may constitute an open low field magnetic resonance device or an enclosed superconducting magnetic resonance device.

The control module 1220 may monitor the MR signal acquisition module 1210 including the magnet unit 1211 and the RF unit 1212, and the processing module 1230. In some embodiments, the control module 1220 may receive information or pulse parameters sent by the MR signal acquisition module 1210. In addition, the control module 1220 may also control data processing of the processing module 1230. In some embodiments, the control module 1220 may further connect to a pulse sequence generator, a gradient waveform generator, a transmitter, a receiver, etc., and execute corresponding scan sequences after an instruction is received from a controller.

Merely for illustration purposes, the MR scanner 1110 may generate MR data (i.e., MR imaging data) in a scanning process in which one or more of the following operations are performed. The main magnet may generate a main magnetic field $B_0$, and nuclei in the body of the subject may have a precession frequency under the main magnetic field, and the precession frequency may be proportional to a magnetic field intensity of the main magnetic field. The control module 1220 may store and transmit instructions encoding a scan sequence to be executed. The pulse sequence generator may control the gradient waveform generator and the transmitter according to the instructions. The gradient waveform generator may output a gradient pulse signal having a predetermined time sequence and waveform. The gradient pulse signal may pass through the gradient current amplifiers, and the three independent channels $G_x$, $G_y$, and $G_z$ in the gradient components. Each gradient amplifier may excite one of the gradient coils, and generate a gradient field for producing spatial encoding signals so as to locate a magnetic resonance signal in a 2D or 3D space. The pulse sequence generator may execute scan sequences, and output data including a transmitting time, an intensity, a shape, etc. of each RF pulse, a receiving time of each RF signal, and a length of a data acquisition window to the transmitter. At the same time, the transmitter may transmit a corresponding RF pulse to one or more body coils in the RF unit 1212 to generate a $B_1$ field. Signals from nuclei in the body of the subject excited by the $B_1$ field may be received by receiving coils in the RF unit 1212, transmitted to the processing module 1230 through transmitting/receiving switches, digitized using amplification, demodulation, filtration, AD conversion, etc., and transmitted to the data storage module 1240. After the storage module 1240 acquires a set of original k-space data, the scanning process may terminate. The set of original k-space data may be rearranged into a plurality of k-space data sets, each of which may correspond to an image to be reconstructed. Each k-space data set may be input into an array processor for image reconstruction, and a set of image data may be generated.

Figure 12B:
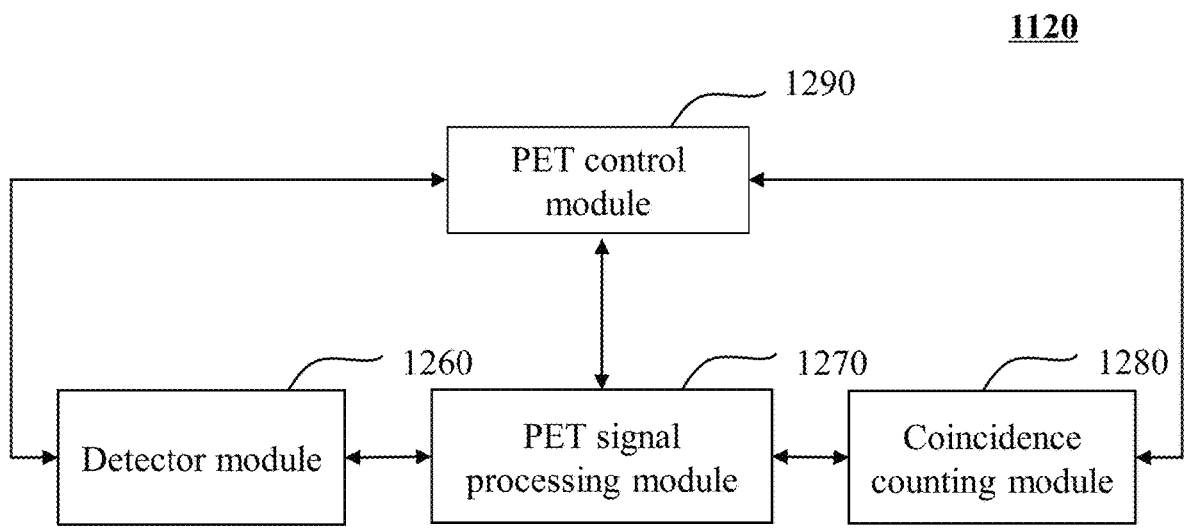
FIG. 12B is an exemplary block diagram of a PET scanner according to some embodiment of the present disclosure.

FIG. 12B is an exemplary block diagram of a PET scanner according to some embodiment of the present disclosure. The PET scanner 1120 may generate PET data (i.e., PET imaging data) of the examination region. The PET scanner 1120 may include a detector module 1260, a PET signal processing module 1270, a coincidence counting module 1280, and a PET control module 1290. The detector module 1260 may include a series of detector units. The series of detector units may be arranged along a central axis of a gantry of the PET scanner 1120 to form a plurality of detector rings. A subject P may be imaged within a field of view (FOV) formed by the plurality of detector rings. Merely for illustration purposes, the PET scanner 1120 may generate PET data in a scanning process in which one or more of the following operations are performed. Agents labeled with radionuclides (i.e., tracers) may be introduced into the subject P prior to a PET scan. An annihilation may occur when a positron collides with an electron. The annihilation may produce a pair of gamma photons. The plurality of detector units may detect multiple pairs of gamma photons emitted from the subject P, and generate pulse shaped electrical signals corresponding to the count of detected pairs of gamma photons. The pulse shaped electrical signals may be transmitted to the PET signal processing module 1270. The PET signal processing module 1270 may generate single event data based on the electrical signals. In some embodiments, the PET signal processing module 1270 may determine the count of the detected pairs of gamma photons according to determinations that whether intensities of the pulse shaped electrical signals exceed a threshold. The single event data may be provided to the coincidence counting module 1280. The coincidence counting module 1280 may perform simultaneous counting operations on the single event data related to multiple single events. In some embodiments, the coincidence counting module 1280 may determine event data of two single events occurred within a predetermined time range from the provided single event data. The time range may be set to, for example, about 6 nanoseconds to 18 nanoseconds. The two single events may be deemed to be a result of an annihilation. The line connecting two detector units that detect the two single event may be defined as a LOR. Coincidence data corresponding to the LOR may be PET data.

An agent labeled with a radionuclide may be a reversible tracer or an irreversible tracer. The PET scan may be a single tracer scan or a multi-tracer dynamic scan. In some embodiments, the head of the subject may be selected as the examination region, and the PET scan may be a dual-tracer dynamic scan. The tracers may include a first tracer $I_1$ and a second tracer $I_2$. The second tracer $I_2$ may be injected at a time point $T_0$. The first tracer may be a reversible tracer, such as 13N—$NH_3$, and the second tracer may be an irreversible tracer, such as 18F-FDG. The dynamic PET scan may start from a time point t=0. The first tracer $I_1$ may be injected into the subject at t=0. The second tracer $I_2$ may be injected at a time point t=$T_0$, and the PET scan may complete after a time period $T_1$. The duration of the entire dynamic PET scan may be $T_0+T_1$. During the dynamic PET scan, detectors may be used to detect radioactive signals emitted from the head of the subject in real-time in which tracers are injected, and original coincidence data may be generated. The acquisition frequency of the original coincidence data may be once per unit time, and $T_0+T_1$ groups of coincidence counting may be obtained. The $T_0$ groups of coincidence counting obtained in the time period $T_0$ may correspond to the first tracer $I_1$, and the $T_1$ groups of coincidence counting obtained in the time period $T_1$ may correspond to the first tracer $I_1$ and the second tracer $I_2$.

In some embodiments, the MR scanner 1110 and the PET scanner 1120 may obtain imaging information of the subject independently. In some embodiments, the MR scanner 1110 and the PET scanner 1120 may be configured as a multi-modality imaging apparatus. In some embodiments, the MR scanner 1110 and the PET scanner 1120 may constitute a PET-MR imaging apparatus. The PET-MR imaging apparatus may include an RF coil support. The RF unit 1212 including a plurality of RF coils may be fixed to an outer surface of the RF coil support. The detector module 1260 may be set around the outer surface of the RF coil support having RF coils, and a shielding layer may be set between PET detectors and the RF coils. Both the RF unit 1212 and the detector module 1260 may be located inside an aperture of the main magnet.

Figure 13:
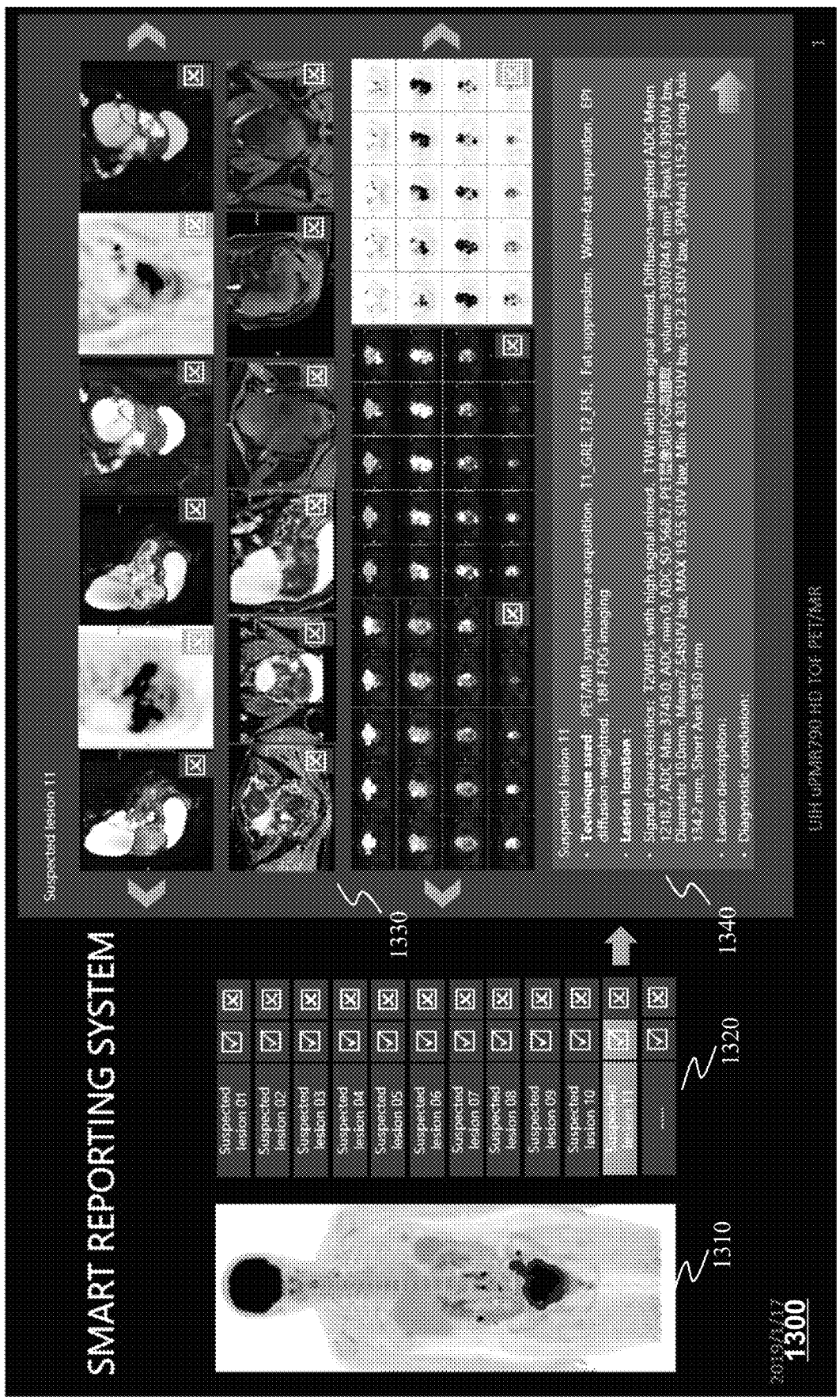
FIG. 13 is a schematic diagram illustrating a reporting interface of the imaging report generation system according to some embodiments of the present disclosure.

FIG. 13 is a schematic diagram illustrating a reporting interface of the imaging report generation system according to some embodiments of the present disclosure. As illustrated in FIG. 13, the reporting interface may include an interaction area and a displaying area. The displaying area may include a first displaying area 1310 and a report displaying area 1340. The interaction area may include a first interaction area 1320 and a second interaction area 1330. The first displaying area 1310 may be arranged at the leftmost side of the reporting interface. First displaying area 1310 may display first imaging information, for example, a PET image. The processing device 120 or the imaging processor 1130 may identify at least one first region automatically in each of which a suspected lesion may be located according to pixels of the PET image. Referring to the PET image, pixels of the head of the subject may differ from those of tissue surrounding the head of the subject. However, the pixels of the head may be evenly distributed overall. The processing device 120 or the imaging processor 1130 may determine the tissue of the head of the subject as normal tissue. Only if pixels in an enclosed region that are dramatically distinguished from pixels of same tissue, the tissue in the region may be determined as a suspected lesion. A plurality of icons corresponding to suspected lesions in the PET image may be arranged in the first interaction area 1320. The first interaction area 1320 may be displayed at the right side of the PET image. A user (e.g., a physician) may select a suspected lesion using a icon and determine whether the suspected lesion is a real lesion or a suspected lesion of interest. When the user selects, from the list of icons in the first interaction area 1320, an icon which corresponds to a suspected lesion, a contour of the suspected lesion may be highlighted, for example, in a particular color, in the at least one image in the first displaying area 1310 simultaneously. At the same time, first imaging information (e.g., PET images) of the suspected lesion, second imaging information (e.g., MR images) of the suspected lesion, and/or fused imaging information of the suspected lesion (e.g., fused images of the PET images and the MR images) may be displayed in the second interaction area 1330.

In some embodiments, the user may further determine whether the suspected lesion is a real lesion or a suspected lesion of interest based on the first imaging information of the suspected lesion, the second imaging information of the suspected lesion, and/or the fused imaging information of the suspected lesion in the second interaction area 1330, in which a variety of images are provided for clinical diagnosis.

In some embodiments, the second interaction area 1330 may display a variety of images in different scales. The different scales may be set by a user, by the imaging report generation system 100 according to default settings of the imaging report generation system 100, etc.

In some embodiments, the second interaction area 1330 may include two or more sub-areas. The first imaging information of the suspected lesion, the second imaging information of the suspected lesion, and/or the fused imaging information of the suspected lesion may be displayed in the two or more sub-areas of the second interaction area 1330. Merely for illustration purposes, the first imaging information including a first plurality of PET images of the suspected lesion may be displayed in one or more rows in a first sub-area of the second interaction area 1330, and the second imaging information including a second plurality of MR images of the suspected lesion may be displayed, in one or more rows, in a second sub-area of the second interaction area 1330. In some embodiments, the user may change the position of the first plurality of PET images and/or the second plurality of MR images in the first sub-area and the second sub-area. For example, a doctor may adjust a position of an MR image from an end position of a second row to a start position of a first row in the second sub-area since the MR image provides a significant characteristic of the suspected lesion. In some embodiments, the user may delete one or more images from the first plurality of PET images and/or the second plurality of MR images by, for example, clicking a cross at a lower right corner of each image. In some embodiments, the user may also add annotations to one or more images of the first plurality of PET images and/or the second plurality of MR images. It should be noted that the user may make various adjustment or modifications to the first imaging information, the second imaging information, and/or the fused imaging information displayed in the second interaction area.

In some embodiments, the report displaying area 1340 may be arranged at the lower right portion of the reporting interface. The reporting displaying area 1340 may display the diagnostic imaging report. The diagnostic imaging report may include at least a part of the first reporting information, the second reporting information, and/or the third reporting information.

In some embodiments, the imaging report generation system 100 may be an insert system that is incorporated into an existing system comprising at least one modality imaging device (e.g., a PET-MR multi-modality imaging device). The insert system may include supporting software for installing on the main system to integrate the insert system with the main system. The reporting interface may serve as a user interface of the integrated system for generating diagnosis reports.

Figure 14:
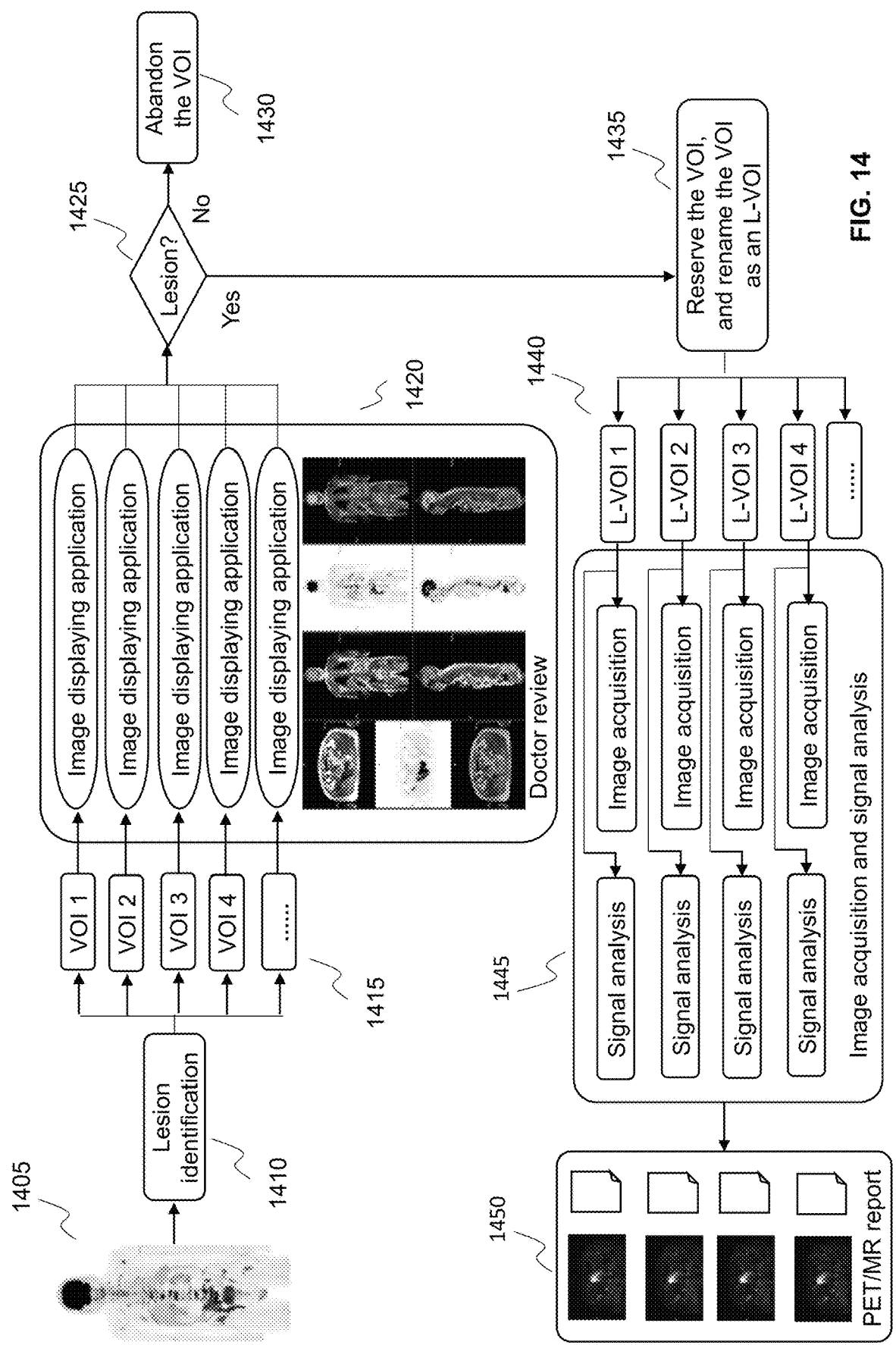
FIG. 14 is a schematic diagram illustrating a process for generating a diagnostic imaging report according to some embodiments of the present disclosure.

FIG. 14 is a schematic diagram illustrating a process for generating an imaging report according to some embodiments of the present disclosure. The imaging report generation system 100 may obtain first imaging information of an examination region of a subject in 1405. The first imaging information may be acquired by a first modality device. The first modality device may include a PET scanner, a SPECT scanner, or the like, or any combination thereof. The first imaging information may include images (e.g., 2D images, 3D images, etc.), videos (e.g., 2D videos, 3D videos, etc.), or the like. Merely by way of example, the first imaging information may include a 3D PET image of the subject.

The imaging report generation system 100 may also obtain second imaging information of the examination region of the subject. The second imaging information may be acquired using a second modality device. The second modality device may include a CT scanner, an MR scanner, an optical scanner, or the like, or any combination thereof. The second imaging information may include an image (e.g., a 2D image, a 3D image, etc.), a video (e.g., a 2D video, a 3D video, etc.), or the like. Merely by way of example, the second imaging information include a plurality of MR images of the subject.

The imaging report generation system 100 may perform a lesion identification in 1410. Since radiation attenuation coefficients and/or physiological metabolism of different types of tissue may be different, gray values between different tissues may be different. In some embodiments, gray values of pixels in a lesion may be different from gray values of pixels surrounding the lesion. In some embodiments, the lesion identification may relate to an image recognition technique. Exemplary image recognition techniques may include a scale-invariant feature transform (SIFT) technique, a speed up robust feature (SURF) technique, a features from accelerated segment test (FAST) technique, etc. The at least one first target ROI may be identified from the PET image using an image recognition technique, such as a scale-invariant feature transform (SIFT) technique, a speed up robust feature (SURF) technique, a features from accelerated segment test (FAST) technique, etc.

The imaging report generation system 100 may determine at least two first volumes of interest (VOIs) in 1415 after the lesion identification operation is performed. In some embodiments, a second VOI corresponding to each of the at least two first VOIs may be determined. In some embodiments, a first VOI and a corresponding second VOI may correspond to a same volume in the subject (i.e., a same part of the body of the subject). In some embodiments, a first VOI and a corresponding second VOI may correspond to different volumes in the subject (i.e., different parts of the body of the subject). The imaging report generation system 100 may cause the first imaging information of each of the at least two first VOIs and second imaging information of a second VOI corresponding to the each of the at least two first VOIs to be displayed in a display device via an image displaying application in 1420. In this way, a doctor may review the first imaging information of the at least two first VOIs and the second imaging information of the second VOI corresponding to the each of the at least two first VOIs displayed on the display device. The doctor may determine whether each of the at least two first VOIs is a suspected lesion in 1425. If a first VOI is not a suspected lesion, the first VOI may be abandoned in 1430. If a first VOI is a suspected lesion, the first VOI may be reserved and renamed as an L-VOI in 1435. In some embodiments, an L-VOI may be designated as a suspected lesion. After the doctor reviews the at least two first VOIs, at least one L-VOI may be determined in 1440.

The imaging report generation system 100 may obtain one or more images (e.g., PET images) of the at least one L-VOI and/or one or more images (e.g, MR images) of at least one second VOI corresponding to the at least one L-VOI, and analyze characteristics of signals of the at least one L-VOI and/or the at least one second VOI corresponding to the at least one L-VOI in 1445. The characteristics of signals of the at least one L-VOI and/or the at least one second VOI corresponding to the at least one L-VOI may include a waveform, an amplitude, a frequency, a peak value, etc.

The imaging report generation system 100 may generate a diagnostic imaging report (e.g., a PET/MR report) in 1450 based on the one or more images of the at least one L-VOI, one or more images of at least one second VOI corresponding to the at least one L-VOI, and/or characteristics of signals of the at least one L-VOI and/or the at least one second VOI. In some embodiments, the diagnostic imaging report may further include locations of lesions, techniques used, detailed descriptions of lesions, a diagnosis conclusion, etc.

In some embodiments, a storage medium storing computer readable instructions for generating a diagnostic imaging report when executed by a processor is provided in the present disclosure. The method may include obtaining first imaging information and second imaging information, wherein the first imaging information is acquired from an examination region of a subject using a first modality device, and the second imaging information is acquired from the examination region of the subject using a second modality device, identifying at least one first target region of interest (ROI) based on the first imaging information, and determining first reporting information corresponding to the at least one first target ROI, identifying at least one second target ROI with respect to the second imaging information based on the at least one first target ROI, and determining second reporting information corresponding to the at least one second target ROI, and generating a diagnostic imaging report based on at least one of the first reporting information and or the second reporting information.

In some embodiments, the computer readable instructions stored in the storage medium are not limited. Instructions related to other operations for generating a diagnostic imaging report may also be provided.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing apparatus having at least one processor and at least one computer-readable storage device, the method comprising:
   obtaining first imaging information and second imaging information, wherein the first imaging information is acquired from an examination region of a subject using a first imaging device, and the second imaging information is acquired from the examination region of the subject using a second imaging device;
   identifying at least one first target region of interest (ROI) based on the first imaging information;
   determining first reporting information corresponding to the at least one first target ROI;
   identifying at least one second target ROI with respect to the second imaging information based on the at least one first target ROI wherein the at least one first target ROI is selected from at least two candidate ROIs, the at least one first target ROI is identified based on a first target ROI determination model, and the first target ROI determination model is generated by:
      designating one or more regions in the at least two candidate ROIs other than the selected at least one first target ROI as filtered-out regions; and
      training a preliminary model based on the filtered-out regions and at least one first target ROI;
   determining second reporting information corresponding to the at least one second target ROI; and
   generating a report based on at least a part of the first reporting information or the second reporting information.

2. The method of claim 1, further including:
   receiving third reporting information input by a user through a user interface; and
   updating the report based on the third report information.

3. The method of claim 1, further including: causing a certain region of the subject to be displayed in a first displaying area of a reporting interface; causing the at least two candidate ROIs to be displayed in the first displaying area and a first interaction area of the reporting interface; causing at least a portion of the first imaging information and the second imaging information to be displayed in a second interaction area of the reporting interface in response to the region selection instruction, the at least a portion of the first imaging information and the second imaging information including information corresponding to the certain region of the subject; and causing the report to be displayed in a report displaying area in the reporting interface.

4. The method of claim 1, training the preliminary model based on the filtered-out regions and at least one first target ROI including:
   determining characteristics of signals related to the filtered-out regions and at least one first target ROI; and
   training the preliminary model based on the characteristics of signals related to the filtered-out regions and at least one first target ROI.

5. The method of claim 1, the identifying at least one first target ROI in the scanning region based on the first imaging information including:
   determining the at least two candidate ROIs in the scanning region based on the first imaging information and an image recognition technique; and
   determining the at least one first target ROI by inputting the at least two candidate ROIs into a first target ROI determination model.

6. The method of claim 1, the obtaining first imaging information including:
   obtaining original imaging information, wherein the original imaging information is acquired from the examination region of the subject using the first imaging device; and
   determining the first imaging information in the original imaging information according to a filtering rule input by a user.

7. The method of claim 1, wherein the first imaging information reflects molecular functional information of the examination region, and the second imaging information reflects anatomical information of the examination region.

8. The method of claim 1, wherein the first imaging information and the second imaging information are with respect to a same coordinate system.

9. The method of claim 8, the identifying at least one second target ROI with respect to the second imaging information based on the at least one first target ROI including:

performing an image fusion or an image registration between the first imaging information and the second imaging information according to the same coordinate system; and identifying at least one ROI associated with the at least one first target ROI in the second imaging information; and designating the identified at least one ROI associated with the at least one first target ROI as the at least one second target ROI.

10. The method of claim 1, wherein the report includes at least one of an image, text, a video, or an annotation.

11. A system, comprising:
at least one storage device storing a set of instructions; and
at least one processor configured to communicate with the at least one storage device, wherein when executing the set of instructions, the at least one processor is configured to cause the system to perform operations including:
obtaining first imaging information and second imaging information, wherein the first imaging information is acquired from an examination region of a subject using a first imaging device, and the second imaging information is acquired from the examination region of the subject using a second imaging device
identifying at least one first target ROI based on the first imaging information;
determining first reporting information corresponding to the at least one first target ROI;
identifying at least one second target ROI with respect to the second imaging information based on the at least one first target ROI, wherein the first target region of interest (ROI) is selected from at least two candidate ROIs, the at least one first target ROI is identified based on a first target ROI determination model, and the first target ROI determination model is generated by designating one or more regions in the at least two candidate ROIs other than the selected at least one first target ROI as filtered-out regions, and training a preliminary model based on the filtered-out regions and at least one first target ROI;
determining second reporting information corresponding to the at least one second target ROI; and
generating a report based on at least a part of the first reporting information or the second reporting information.

12. The system of claim 11, the at least one processor is further configured to cause the system to perform the operations including: causing a certain region of the subject to be displayed in a first displaying area of a reporting interface; causing the at least two candidate ROIs to be displayed in the first displaying area and a first interaction area of the reporting interface; causing at least a portion of the first imaging information and the second imaging information to be displayed in a second interaction area of the reporting interface in response to the region selection instruction, the at least a portion of the first imaging information and the second imaging information including information corresponding to the certain region of the subject; and causing the report to be displayed in a report displaying area in the reporting interface.

13. The system of claim 11, to identify at least one first target ROI in the scanning region based on the first imaging information, the at least one processor is configured to cause the system to perform the operations including:
determining the at least two candidate ROIs in the scanning region based on the first imaging information and an image recognition technique; and
determining the at least one first target ROI by inputting the at least two candidate ROIs into a first target ROI determination model.

14. A device, comprising:
at least one storage device storing a set of instructions; and
at least one processor configured to communicate with the at least one storage device, wherein when executing the set of instructions, the at least one processor is configured to cause the device to perform the operations including:
obtaining first imaging information and second imaging information, wherein the first imaging information is acquired from an examination region of a subject using a first imaging device, and the second imaging information is acquired from the examination region of the subject using a second imaging device;
identifying at least one first target ROI based on the first imaging information;
determining first reporting information corresponding to the at least one first target ROI;
identifying at least one second target ROI with respect to the second imaging information based on the at least one first target ROI, wherein the first target region of interest (ROI) is selected from at least two candidate ROIs, the at least one first target ROI is identified based on a first target ROI determination model, and the first target ROI determination model is generated by designating one or more regions in the at least two candidate ROIs other than the selected at least one first target ROI as filtered-out regions, and training a preliminary model based on the filtered-out regions and at least one first target ROI; and
generating a report based on at least a part of the at least one first target ROI or the at least one second target ROI.

15. The device of claim 14, further including:
a display interface including at least one displaying area and at least one interaction area, wherein
at least one of the first imaging information, the second imaging information, or the report is displayed on the at least one displaying area;
at least one of the at least one first target ROI or the at least one second target ROI is displayed on the at least one interaction area; and
at least one of the at least one first target ROI or the at least one second target ROI is selected or deleted through the at least one interaction area.

16. The system of claim 11, the at least one processor is further configured to cause the system to perform the operations including:
receiving third reporting information input by a user through a user interface; and
updating the report based on the third report information.

17. The device of claim 14, wherein the first imaging device includes a PET scanner, the second imaging device includes a CT scanner or an MR scanner, and the PET scanner is integrated with the CT scanner or the MR scanner.

* * * * *